(12) United States Patent
Palsule et al.

(10) Patent No.: US 10,196,481 B2
(45) Date of Patent: Feb. 5, 2019

(54) POLYMER AND OTHER COMPOUNDS FUNCTIONALIZED WITH TERMINAL 1,1-DISUBSTITUTED ALKENE MONOMER(S) AND METHODS THEREOF

(71) Applicant: SIRRUS, INC., Loveland, OH (US)

(72) Inventors: Aniruddha Palsule, Cincinnati, OH (US); Jeffrey M. Sullivan, Goshen, OH (US); Kshitij K. Parab, Loveland, OH (US); Ami Doshi, Loveland, OH (US); Alexander R. Holzer, Loveland, OH (US); Matthew Reilman, Cincinnati, OH (US)

(73) Assignee: Sirrus, Inc., Loveland, OH (US)

( * ) Notice: Subject to any disclaimer, the term of this patent is extended or adjusted under 35 U.S.C. 154(b) by 0 days.

(21) Appl. No.: 15/592,829

(22) Filed: May 11, 2017

(65) Prior Publication Data

US 2017/0349700 A1    Dec. 7, 2017

Related U.S. Application Data

(63) Continuation-in-part of application No. 15/437,164, filed on Feb. 20, 2017, now Pat. No. 9,745,413, which is a continuation of application No. 15/234,191, filed on Aug. 11, 2016, now Pat. No. 9,617,377.

(60) Provisional application No. 62/421,754, filed on Nov. 14, 2016, provisional application No. 62/345,334, filed on Jun. 3, 2016.

(51) Int. Cl.
| | |
|---|---|
| *C08G 63/02* | (2006.01) |
| *C08G 63/16* | (2006.01) |
| *B32B 27/36* | (2006.01) |
| *C12P 7/62* | (2006.01) |
| *C08G 63/87* | (2006.01) |
| *C08G 63/52* | (2006.01) |
| *C08G 63/54* | (2006.01) |
| *C08G 63/91* | (2006.01) |
| *C08G 64/42* | (2006.01) |

(52) U.S. Cl.
CPC .............. *C08G 63/16* (2013.01); *B32B 27/36* (2013.01); *C08G 63/52* (2013.01); *C08G 63/54* (2013.01); *C08G 63/87* (2013.01); *C08G 63/916* (2013.01); *C08G 64/42* (2013.01); *C12P 7/625* (2013.01)

(58) Field of Classification Search
USPC ................................................ 528/271, 272
See application file for complete search history.

(56) References Cited

U.S. PATENT DOCUMENTS

| | | |
|---|---|---|
| 2,212,506 A | 8/1940 | Bachman |
| 2,245,567 A | 6/1941 | Brant et al. |
| 2,403,791 A | 7/1941 | D' Aiello |
| 2,277,479 A | 3/1942 | D' Aiello |
| 2,313,501 A | 3/1943 | Bachman et al. |
| 2,330,033 A | 9/1943 | D' Aiello |
| 3,042,710 A | 7/1962 | Dickstein et al. |
| 3,197,318 A | 7/1965 | Halpern et al. |
| 3,203,915 A | 8/1965 | D' Aiello |
| 3,221,745 A | 12/1965 | Coover et al. |
| 3,427,250 A | 2/1969 | Haas et al. |
| 3,489,663 A | 1/1970 | Bayer et al. |
| 3,523,097 A | 8/1970 | Coover et al. |
| 3,557,185 A | 1/1971 | Ito et al. |
| 3,591,676 A | 7/1971 | Hawkins |
| 3,595,869 A | 7/1971 | Shuman |
| 3,677,989 A | 7/1972 | Jenkinson |
| 3,758,550 A | 9/1973 | Eck et al. |
| 3,923,836 A | 12/1975 | Bender |
| 3,936,486 A | 2/1976 | Egger et al. |
| 3,940,362 A | 2/1976 | Overhurlts |
| 3,945,891 A | 3/1976 | Aal et al. |
| 3,966,562 A | 6/1976 | Mukushi et al. |
| 3,975,422 A | 8/1976 | Buck |
| 3,978,422 A | 8/1976 | Rheinfelder |
| 3,995,489 A | 12/1976 | Smith et al. |
| 4,001,345 A | 1/1977 | Gorton et al. |
| 4,004,984 A | 1/1977 | Margen |
| 4,018,656 A | 4/1977 | Rogers et al. |
| 4,035,243 A | 7/1977 | Katz et al. |
| 4,036,985 A | 7/1977 | Amato et al. |
| 4,046,943 A | 9/1977 | Smith et al. |
| 4,049,698 A | 9/1977 | Hawkins et al. |
| 4,056,543 A | 11/1977 | Ponticello |
| 4,079,058 A | 3/1978 | Ackermann et al. |
| 4,080,238 A | 3/1978 | Wolinski et al. |
| 4,083,751 A | 4/1978 | Choi et al. |
| 4,102,809 A | 7/1978 | Smith et al. |
| 4,105,688 A | 8/1978 | Arni et al. |
| 4,140,584 A | 2/1979 | Margen |
| 4,148,693 A | 4/1979 | Williamson |
| 4,154,914 A | 5/1979 | Kuraya |
| 4,160,864 A | 7/1979 | Ponticello et al. |
| 4,176,012 A | 11/1979 | Bryant |
| 4,186,058 A | 1/1980 | Katz et al. |
| 4,186,060 A | 1/1980 | Katz et al. |

(Continued)

FOREIGN PATENT DOCUMENTS

| | | |
|---|---|---|
| CN | 102901754 A | 1/2013 |
| DE | 19508049 A1 | 9/1996 |

(Continued)

OTHER PUBLICATIONS

Takagi et al.: Kogyo Kagaku Zasshi, Reaction of Active Methylene Radicals with Formaldehyde. L. Synthesis of Diethyl Methylenemalonate, 1953, 56, pp. 901-903, English abstract.

(Continued)

*Primary Examiner* — Terressa Boykin

(74) *Attorney, Agent, or Firm* — Young Basile Hanlon & MacFarlane, P.C.

(57) ABSTRACT

Functionalized compounds including residues of one or more 1,1-disubstituted alkene compounds. Preferably the functionalized compound includes the residue of two or more 1,1-disubstituted alkene compounds, which are spaced apart. The functionalized compound may be produced by a transesterification reaction. The functionalized compounds may be employed in a polymerizable composition and may be used to prepare new polymers, (for example by reacting the alkene group).

15 Claims, 10 Drawing Sheets

(56) References Cited

U.S. PATENT DOCUMENTS

| | | |
|---|---|---|
| 4,198,334 A | 4/1980 | Rasberger |
| 4,224,112 A | 9/1980 | Childs |
| 4,229,263 A | 10/1980 | Childs |
| 4,236,975 A | 12/1980 | Childs |
| 4,237,297 A | 12/1980 | Rody et al. |
| 4,243,493 A | 1/1981 | Gruber et al. |
| 4,256,908 A | 3/1981 | Nishimura et al. |
| 4,282,067 A | 8/1981 | Katz et al. |
| 4,282,071 A | 8/1981 | Sherrod |
| 4,291,171 A | 9/1981 | Baum et al. |
| 4,313,865 A | 2/1982 | Teramoto et al. |
| 4,319,964 A | 3/1982 | Katz et al. |
| 4,329,479 A | 5/1982 | Yabutani et al. |
| 4,396,039 A | 8/1983 | Klenk et al. |
| 4,399,300 A | 8/1983 | Prange et al. |
| 4,411,740 A | 10/1983 | Flanigam et al. |
| 4,440,601 A | 4/1984 | Katz et al. |
| 4,440,910 A | 4/1984 | O'Connor |
| 4,443,624 A | 4/1984 | Prange et al. |
| 4,444,928 A | 4/1984 | Karrer |
| 4,450,067 A | 5/1984 | Angevine et al. |
| 4,503,074 A | 3/1985 | Friedman |
| 4,504,658 A | 3/1985 | Narisada et al. |
| 4,510,273 A | 4/1985 | Miura et al. |
| 4,517,105 A | 5/1985 | Laemmle et al. |
| 4,539,423 A | 9/1985 | Itatani et al. |
| 4,556,649 A | 12/1985 | Salzburg et al. |
| 4,560,723 A | 12/1985 | Millet et al. |
| 4,578,503 A | 3/1986 | Ishikawa et al. |
| 4,584,064 A | 4/1986 | Ciais et al. |
| 4,613,658 A | 9/1986 | Mathias et al. |
| 4,698,333 A | 10/1987 | Fauss et al. |
| 4,720,543 A | 1/1988 | McPherson et al. |
| 4,727,701 A | 3/1988 | Figari |
| 4,728,701 A | 3/1988 | Jarvis et al. |
| 4,736,056 A | 4/1988 | Smith et al. |
| 4,767,503 A | 8/1988 | Crescentini et al. |
| 4,769,464 A | 9/1988 | Sajtos |
| 4,783,242 A | 11/1988 | Robbins |
| 4,835,153 A | 5/1989 | Kabota et al. |
| 4,897,473 A | 1/1990 | Dombek |
| 4,914,226 A | 4/1990 | Di Trapani et al. |
| 4,931,584 A | 6/1990 | Bru-Magniez et al. |
| 4,932,584 A | 6/1990 | Yamazaki et al. |
| 5,021,486 A | 6/1991 | Galbo |
| 5,039,720 A | 8/1991 | Saatweber et al. |
| 5,064,507 A | 11/1991 | O'Donnell |
| 5,142,098 A | 8/1992 | Bru-Magniez et al. |
| 5,162,545 A | 11/1992 | Etzbach et al. |
| 5,210,222 A | 5/1993 | O'Murchu |
| 5,227,027 A | 7/1993 | Topper |
| 5,259,835 A | 11/1993 | Clark et al. |
| 5,284,987 A | 2/1994 | Sikkenga et al. |
| 5,292,937 A | 3/1994 | Manning et al. |
| 5,328,687 A | 4/1994 | Leung et al. |
| 5,312,864 A | 5/1994 | Wenz et al. |
| 5,334,747 A | 8/1994 | Steffen |
| 5,426,203 A | 6/1995 | Sohn et al. |
| 5,446,195 A | 8/1995 | Pacifici |
| 5,514,371 A | 5/1996 | Leung et al. |
| 5,514,372 A | 5/1996 | Leung et al. |
| 5,550,172 A | 8/1996 | Regula et al. |
| 5,565,525 A | 10/1996 | Morimoto et al. |
| 5,567,761 A | 11/1996 | Song |
| 5,575,997 A | 11/1996 | Leung et al. |
| 5,582,834 A | 12/1996 | Leung et al. |
| 5,614,650 A | 3/1997 | Sandler et al. |
| 5,624,669 A | 4/1997 | Leung et al. |
| 5,693,621 A | 12/1997 | Toepfer et al. |
| 5,817,742 A | 10/1998 | Toepfer et al. |
| 5,817,870 A | 10/1998 | Haas et al. |
| 5,886,219 A | 3/1999 | Steffen |
| 5,902,896 A | 5/1999 | Bauer |
| 5,952,407 A | 9/1999 | Rasoul et al. |
| 6,054,606 A | 4/2000 | Irie et al. |
| 6,069,261 A | 5/2000 | Hoffmann et al. |
| 6,096,848 A | 8/2000 | Gololobov et al. |
| 6,106,807 A | 8/2000 | Albayrak et al. |
| 6,143,352 A | 11/2000 | Clark et al. |
| 6,183,593 B1 | 2/2001 | Narang et al. |
| 6,210,474 B1 | 4/2001 | Romano, Jr. et al. |
| 6,211,273 B1 | 4/2001 | Bru-Magniez et al. |
| 6,225,038 B1 | 5/2001 | Smith et al. |
| 6,238,896 B1 | 5/2001 | Ozaki et al. |
| 6,245,933 B1 | 6/2001 | Malofsky et al. |
| 6,284,915 B2 | 9/2001 | Hirase et al. |
| 6,291,703 B1 | 9/2001 | Schaerfl et al. |
| 6,376,019 B1 | 4/2002 | Leung |
| 6,395,737 B1 | 5/2002 | Defossa et al. |
| 6,395,931 B1 | 5/2002 | Carvalho et al. |
| 6,413,415 B1 | 7/2002 | Weiss et al. |
| 6,420,468 B2 | 7/2002 | Bru-Magniez et al. |
| 6,440,461 B1 | 8/2002 | Bru-Magniez et al. |
| 6,512,023 B1 | 1/2003 | Malofsky et al. |
| 6,518,677 B1 | 2/2003 | Capote |
| 6,545,097 B2 | 4/2003 | Pinchuk et al. |
| 6,559,264 B1 | 5/2003 | Konig et al. |
| 6,610,078 B1 | 8/2003 | Bru-Magniez et al. |
| 6,613,934 B1 | 9/2003 | Jegelka et al. |
| 6,673,957 B2 | 1/2004 | Bartek et al. |
| 6,699,928 B2 | 3/2004 | Cobbley et al. |
| 6,716,355 B1 | 4/2004 | Hanemaaijer et al. |
| 6,750,298 B1 | 6/2004 | Bru-Magniez et al. |
| 6,794,365 B2 | 9/2004 | Al-Obeidi et al. |
| 6,841,064 B1 | 1/2005 | Weiss et al. |
| 6,936,140 B2 | 8/2005 | Paxton et al. |
| 7,070,675 B2 | 7/2006 | Schmidt et al. |
| 7,109,369 B2 | 9/2006 | Nose et al. |
| 7,208,621 B2 | 4/2007 | Nose et al. |
| 7,226,957 B1 | 6/2007 | Scranton et al. |
| 7,305,850 B2 | 12/2007 | Tonkovich et al. |
| 7,553,989 B2 | 6/2009 | Sawabe et al. |
| 7,603,889 B2 | 10/2009 | Cypes et al. |
| 7,610,775 B2 | 11/2009 | Tonkovich et al. |
| 7,649,108 B2 | 1/2010 | Schal et al. |
| 7,659,423 B1 | 2/2010 | McArdle |
| 7,663,000 B2 | 2/2010 | Dekkers et al. |
| 7,771,567 B2 | 8/2010 | Rives et al. |
| 7,829,738 B2 | 11/2010 | Brammer et al. |
| 7,900,558 B2 | 3/2011 | Yokoi |
| 8,425,999 B2 | 4/2013 | McArdle et al. |
| 8,609,885 B2 | 12/2013 | Malofsky et al. |
| 8,884,051 B2 | 11/2014 | Malofsky et al. |
| 9,108,914 B1 | 8/2015 | Malofsky et al. |
| 9,181,365 B2 | 11/2015 | Malofsky et al. |
| 9,217,098 B1 | 12/2015 | Stevenson et al. |
| 9,221,739 B2 | 12/2015 | Malofsky et al. |
| 9,234,107 B2 | 1/2016 | Malofsky et al. |
| 9,334,430 B1 | 5/2016 | Stevenson et al. |
| 9,481,640 B2 | 11/2016 | McArdle et al. |
| 2001/0005572 A1 | 6/2001 | Lobo et al. |
| 2001/0034300 A1 | 10/2001 | Yurugu et al. |
| 2002/0035231 A1 | 3/2002 | Whitehouse et al. |
| 2002/0143128 A1 | 10/2002 | Cabioch et al. |
| 2002/0151629 A1 | 10/2002 | Buffkin et al. |
| 2003/0096069 A1 | 5/2003 | D' Alessio |
| 2003/0199655 A1 | 10/2003 | Yurugi et al. |
| 2004/0057914 A1 | 3/2004 | Bonda et al. |
| 2004/0076601 A1 | 4/2004 | Bru-Magniez et al. |
| 2004/0082043 A1 | 4/2004 | Yadav et al. |
| 2004/0220060 A1 | 11/2004 | Bartley et al. |
| 2006/0167267 A1 | 7/2006 | Chorghade et al. |
| 2006/0211809 A1 | 9/2006 | Kodemura et al. |
| 2007/0043145 A1 | 2/2007 | Beck et al. |
| 2007/0049655 A1 | 3/2007 | Yoshimune et al. |
| 2007/0092483 A1 | 4/2007 | Pollock |
| 2007/0120630 A1 | 5/2007 | Malofsky et al. |
| 2007/0238872 A1 | 10/2007 | Sabesan |
| 2008/0131618 A1 | 6/2008 | Nakamura et al. |
| 2008/0160305 A1 | 7/2008 | Warren et al. |
| 2008/0187655 A1 | 8/2008 | Markle et al. |
| 2008/0227919 A9 | 9/2008 | Li et al. |
| 2008/0241485 A1 | 10/2008 | Shimomura et al. |
| 2008/0286333 A1 | 11/2008 | Kangas et al. |

(56) References Cited

U.S. PATENT DOCUMENTS

| | | | |
|---|---|---|---|
| 2009/0203861 A1 | 8/2009 | Lee et al. | |
| 2009/0263604 A1 | 10/2009 | Arai et al. | |
| 2010/0016508 A1 | 1/2010 | Sasagawa et al. | |
| 2010/0256720 A1 | 10/2010 | Overstreet et al. | |
| 2010/0286433 A1 | 11/2010 | Malofsky et al. | |
| 2010/0286438 A1 | 11/2010 | Malofsky et al. | |
| 2011/0015406 A1 | 1/2011 | Umetani et al. | |
| 2011/0024392 A1 | 2/2011 | Sato et al. | |
| 2011/0164322 A1 | 7/2011 | Morozumi et al. | |
| 2012/0083523 A1 | 4/2012 | Richard et al. | |
| 2012/0136130 A1 | 5/2012 | Takashima et al. | |
| 2012/0203021 A1 | 8/2012 | Friese et al. | |
| 2013/0019520 A1 | 1/2013 | Sello et al. | |
| 2013/0281580 A1 | 10/2013 | Malofsky et al. | |
| 2013/0303719 A1 | 11/2013 | Malofsky et al. | |
| 2013/0324754 A1 | 12/2013 | Bredsguard | |
| 2014/0058031 A1 | 2/2014 | Overbeek et al. | |
| 2014/0248485 A1 | 9/2014 | Malofsky et al. | |
| 2014/0275400 A1 | 9/2014 | Chen et al. | |
| 2014/0288230 A1 | 9/2014 | Malofsky et al. | |
| 2014/0329980 A1* | 11/2014 | Malofsky | C09J 133/06 526/309 |
| 2015/0056879 A1 | 2/2015 | Malofsky et al. | |
| 2015/0104660 A1 | 4/2015 | Malofsky et al. | |
| 2015/0148480 A1 | 5/2015 | Ellison et al. | |
| 2015/0210894 A1 | 7/2015 | Malofsky et al. | |
| 2015/0303122 A1 | 10/2015 | Malofsky et al. | |
| 2015/0361283 A1 | 12/2015 | Malofsky et al. | |

FOREIGN PATENT DOCUMENTS

| | | | |
|---|---|---|---|
| EP | 2768917 | A2 | 2/2009 |
| FR | 2788516 | A1 | 7/2000 |
| GB | 432628 | A | 7/1935 |
| GB | 965676 | | 8/1964 |
| GB | 965767 | | 8/1964 |
| GB | 975733 | | 11/1964 |
| JP | S56-081537 | A | 7/1981 |
| JP | H02281013 | | 11/1990 |
| JP | H08231564 | | 9/1996 |
| JP | 09258448 | A | 10/1997 |
| JP | 2000199936 | A | 7/2000 |
| JP | 2003201397 | A | 7/2003 |
| JP | 2008174494 | | 1/2007 |
| WO | 1999/046619 | | 9/1999 |
| WO | 1999/055394 | A1 | 11/1999 |
| WO | 2007/120630 | A2 | 10/2007 |
| WO | 2010/091975 | A1 | 8/2010 |
| WO | 2010/129068 | A1 | 11/2010 |
| WO | 2011/059104 | A1 | 5/2011 |
| WO | 2011/161045 | A1 | 12/2011 |
| WO | 2012/054616 | A2 | 4/2012 |
| WO | 2012/054633 | A2 | 4/2012 |
| WO | 2013/059473 | | 4/2013 |
| WO | 2013/066629 | | 5/2013 |
| WO | 2013/149165 | A1 | 10/2013 |
| WO | 2013/149168 | A1 | 10/2013 |
| WO | 2013/149173 | A1 | 10/2013 |

OTHER PUBLICATIONS

McNab, Kirk-Othmer Encyclopedia of chemical Technology, Pyrolysis, Flash Vacuum, 2009, John Wiley & Sons, Inc., pp. 1-26.
Block, "Diethyl bis (hydroxymethyl) malonate" Organic Syntheses, 1973, Coll. vol. 5, p. 381 [vol. 40, p. 27 (1960); Retrieved on Apr. 4, 2014 from internet: http://www.Orgsyn.org/content/pdfs/procedures/cv5p0381.pdf] p. 381, para 1.
Reddy et al. "An easy-to-use heterogeneous promoted zirconia catalyst for Knoevenagel condensation in liquid phase under solvent-free conditions." Journal of Molecular Catalysts A: Chemical 258 (2006) pp. 302-307.
M. Ware et al.: "DBU: An Efficient Catalyst for Knoeveganel Condensation under Solvent-free Condition," Bulletin of the Catalysis Society of India, (2007), vol. 6, pp. 104-106.
V. G. Nenajdenko et al.: "Reaction of 2-Methylene-1,3-Dicarbonyl Compounds Containing a CF3-Group with 1,3-Dienes," Tetrahedron, (2000), vol. 56, pp. 6549-6556.
J. S. Yadav et al.,: "Phosphane-Catalyzed Knoevenagel Condensation: a Facile Synthesis of a-Cyanoacrylates and a-Cyanoacrylonitriles," Eur, J, Org, Chem. (2004), pp. 546-551.
B. C. Ranu et al.: "Ionic Liquid as Catalyst and Reaction Medium—a Simple, Efficient and Green Procedure for Knoevenagel Condensation of Aliphatic and Aromatic Carbonyl Compounds Using a Task-Specific Basic Ionic Liquid," Euro. J. Org <http://Euro.J.Org>. Chem., (2006), pp. 3767-3770.
H, A, Oskooie et al.: "On Water: an Efficient Knoevenagel Condensation using 12-Tungstophosphoric Acid as a Reusable Green Catalyst," Synthetic Communications, (2006), vol. 36, pp. 2819-2823.
H. Jiang et al.: "Inorganic Zinc Salts Catalyzed Knoevenagel Condensation at Room Temperature without Solvent," Preparative Biochemistry & Biotechnology, (2009), vol. 39, pp. 194-200.
T. Doi et al.: "Synthesis of Dimethyl gloiosiphne A by Way of Palladium-Catalyzed Domino Cyclization," T. Ora <htto://T.Ora>. Chem., (2007), vol. 72, pp. 3667-3671.
H. Jung et al,: "New and General Methods for the Synthesis of Arylmethylene Bis(3-Hydroxy-2-Cyclohexene-1-0nes) and Xanthenediones by EDDA and In(OTf)3-Catalyzed One-Pot Domino Knoevenagei/Michael or Koevenagei/Michael/Cyclodehydration Reactions," Bull. Korean Chem. Soc. (2009) vol. 30, No, 9, pp. 1989-1995.
P. Klemarczyk: "Adhesion Studies of Mixtures of Ethyl Cyanoacrylate with a Difunctional Cyanoacrylate Monomer and with other Electron-deficient Olefins," J. Adhesion, (1999), vol. 69, pp. 293-306.
P. Klemarwczyk: "A General Synthesis of 1,1 Disubstituted Electron Deficient Olefins and their Polymer Properties," Polymer,- (1998), vol. 39, No, I, pp. 173-181.
Gill, Charansingh, et al. "Knoevenagel condensation in neutral media: a simple and efficient protocol for the synthesis of electrophilic alkenes catalyzed by anhydrous ferric sulphate with remarkable reusability." Bulletin of the Catalysis Society of India 7 (2008): 153-157.
P, Ballesteros et al.: "D 1-tert-Butyl Methylenemalonate [Propanedioic Acid, Methylene-, bis( 1,1-dimethylethyl)ester]," Organic Syntheses. Coli. (1990), vol. 7, p. 142; (1986) vol. 64, p. 63.
A. M. Vetrova et al.: "Improvement of the Thermal Stability of Cyanoacrylate Adhesives," Polymer Science, Series D, (2009), vol. 2, No. 1, pp. 27-30.
A. C. Cope: "Condensation Reactions. I. The Condensation of Ketones with Cyanoacetic Esters and the Mechanism of the Knoevenagel Reaction," Condensation of Ketones with Cyanoacetic Esters, (1937), vol. 59, pp. 2327-2330.
G. Lai et al.: "Ionic Liquid Functionalized Silica Gel: Novel Catalyst and Fixed Solvent," Tetrahedron Letters (2006), vol. 47, pp. 6951-6953.
J. R. Harjani et al.: "Lewis Acidic Ionic Liquids for the Synthesis of Electrophilic Alkenes; via the Knoevenagel Condensation," Tetrahedron Letters, (2002), vol. 43, pp. 1127-1130.
P. Ballesteros et al.: "Synthesis of D1-tent-Butyl Methylenemalonate, a Sterically Hindered 1,1-Dicarbonyl Alkene," J. Ora <htto://J.Ora>. Chem, (1983), vol. 48, pp. 3603-3605.
M. Matziari et al. Active Methylene Phosphinic Peptides: A new Diversification Approach Organic Letters 2006 vol. 8, No. 11 pp. 2317-2319 May 5, 2006.
Zaragoza Dorwald, Side Reactions in Organic Synthesis, 2005, WILEY-VCH Verlag GmbH & Co., KgaA, Weinheim, Preface. p. IX.
K. Okamura and T. Date, A Facile Conversion of Ethoxydihydropyrans to 4-Cyanoethylisoxazoles, J. Heterocyclic Chem. 33, 383 (1996).
Yamauchi et al. Tetrahedron Asymetry 12, (2001), 3113-3118.
Cristoph Schotes et al. "Cu(I)- and C(II)-Catalyzed Cyclo- and Michael Addition Reactions of Unsaturated [beta]-Ketoesters" The Journal of Organic Chemistry, vol. 76, No. 14 dated Jul. 15, 2011 p. 5862-5866.

(56) References Cited

OTHER PUBLICATIONS

Alejandro Bugarin et al. "Efficient direct [alpha]-methylenation of carbonyls mediated by dissopropylammonium trifluoroacetate", Chemical Communications, vol. 46, No. 10 dated Jan. 25, 2010.

H. Hoffman et al. "Preparation and Selected Reaction of tery-Butyl 2-Methylene-3-oxoalkanoates" Chem. Ber., vol. 124 dated Jan. 1, 1991, pp. 2475-2480.

M. Yamauchi et al. "Reactivity of 2-Methylene-1, 3-dicarbonyl Compounds. 1,3-Dipolar Cycloaddition Reaction with Ethyl Diazoacetate", Chem. Pham. Bull., vol. 49, No. 12, dated Jun. 25, 2001, pp. 1638-1639.

Lawrence N J et al. "Reaction of Baylis-Hillman products with Swern and Dess-Martin oxidants", Tetrahedron Letters, Pergamon, GB, vol. 42 No. 23 dated Jun. 4, 2001, pp. 3939-3941.

Juliana Vale et al. "Efficient [alpha]-Methylenation of Carbonyl Compounds in Ionic Liquids at Room Temperature", Synlett, vol. 2009, No. 01, Jan. 1, 2009 (Jan. 1, 2009), pp. 75-78, XP055170349, ISSN: 0936-5214, DOI: 10.1055/s-0028-1087389 *table 2; compound 3 *.

P. Breton et al., "New Poly(Methylidudene Malonate 2.1.2) Nanoparticles: Recent Developments", Targeting of Drugs 4, NATO ASI Series, vol. 273, pp. 161-172, 1994.

Limouzin et al., "Anionic Polymerization of n-Butyl Cyanoacrylate in Emulsion and Miniemulsion" Macromolecules, vol. 36, 2003, pp. 667-674.

McCoy, M. "A New Way to Stick" Chemical & Engineering News, vol. 92, Issue 26, Jun. 30, 2014, pp. 17-18, paragraph [2].

Bachman et al., "Diethyl Methylenemalonate" Contirbution from the Research Laboratories of the Eastman Kodak Company, May 17, 1939, pp. 493-501.

"Knoevenagel reaction on a molecular sieve", Li Qifang et al., Chinese Science Bulletin, vol. 12, pp. 914-917. (1988).

"Knoevenagel Condensation Over Acidic Zeolite", Zuo Bojun et al., Chinese Journal ofCatalysis, vol. 23 (6), pp. 555-558. (2002).

"Comparison of the catalytic activity of MOFs and zeolites in Knoevenagel condensation", Maksym Opanasenko, et al., Catalysis Science & Technology, vol. 3 p. 500-507. (2013).

Corey et al. "Total Synthesis of Gibberellic Acid. A Simple Synthesiss of a Key Intermediate", J. Am. Chem. Soc. 1982, 104, 6129-6130.

Krishna et al. "Stereodefined Access to 3-Deoxy Sugars Through a Tandem Baylis-Hillman and Lewis Acid Catalyzed Sequence", European Journal of Organic Chemistry, 2010, 813-817.

March, *Advanced Organic Chemistry*, 2d Ed, section 0-25, pp. 365-367, 1977, McGraw Hill, New York, New York.

Morrison and Boyd, *Organic Chemistry*, $4^{th}$ Ed., pp. 831 and 836-838, 1983, Allyn Bacon, Inc., Boston, MA.

Otera et al., "Esterification: Methods, Reactions, and Applications", $2^{nd}$ Ed., pp. 55-58, 2010, WILEY-VCH Verlag Gmbh & Co. KGaA. Weinheim, Germany.

"Esterification of Sludge Palm Oil Using Trifluromethanesulfonic Acid for Preparation of Biodiesel Fuel", Korean Journal of Chemical Engineering, Jun. 2013, vol. 30, issue 6, pp. 1229-1234.

Transsesterification of diethyl malonate with Benzyl Alcohol Catalyzed by Modified Zirconia: Kinetic Study, Journal of Molecular Catalysis A: Chemical, vol. 391, Sep. 2014, pp. 55-65.

Olah et al., "Superelectrophilic Solvation," Accounts of Chemical Research, Apr. 2004, vol. 37, No. 4.

Kütt et al., "Equilibrium Acidities of Superacids," Journal of Organic Chemistry, vol. 76, No. 2, 2011, pp. 391-395, published on the web Dec. 17, 2010.

Larras et al. Synthesis and micellization of amphiphilic poly(ethylene oxide)-block-poly(methylidene malonate 2.1.2.) diblock copolymers Macromol. Rapid Commun. dated2000, vol. 21, pp. 1089-1029.

Yamauchi et al. *A Facile Conversion of Ethoxydihydropyrans to 4-Cyanoethylisoxazoles*, Mar.-Apr. 1996, pp. 383-387.

* cited by examiner

FIG. 1C. Typical NMR acquisition parameters

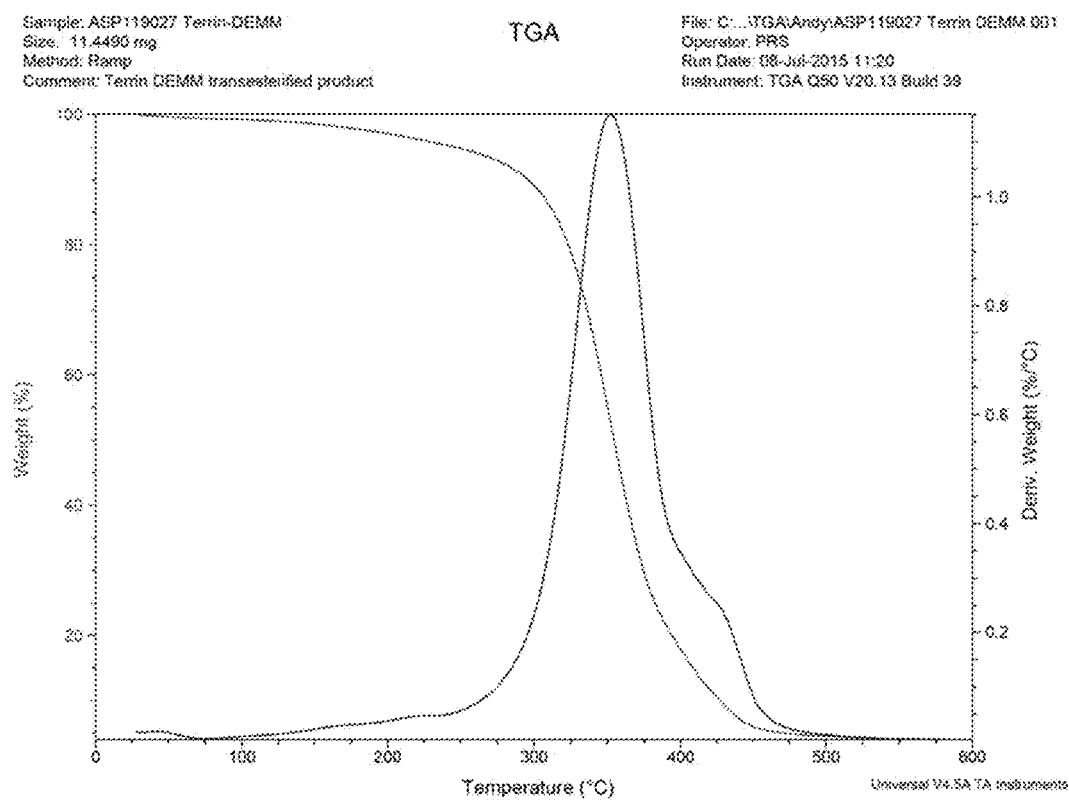
FIG. 2: Thermogravimetric Analysis (TGA) of DEMM crosslinked with end capped Terrin aliphatic polyester polyol

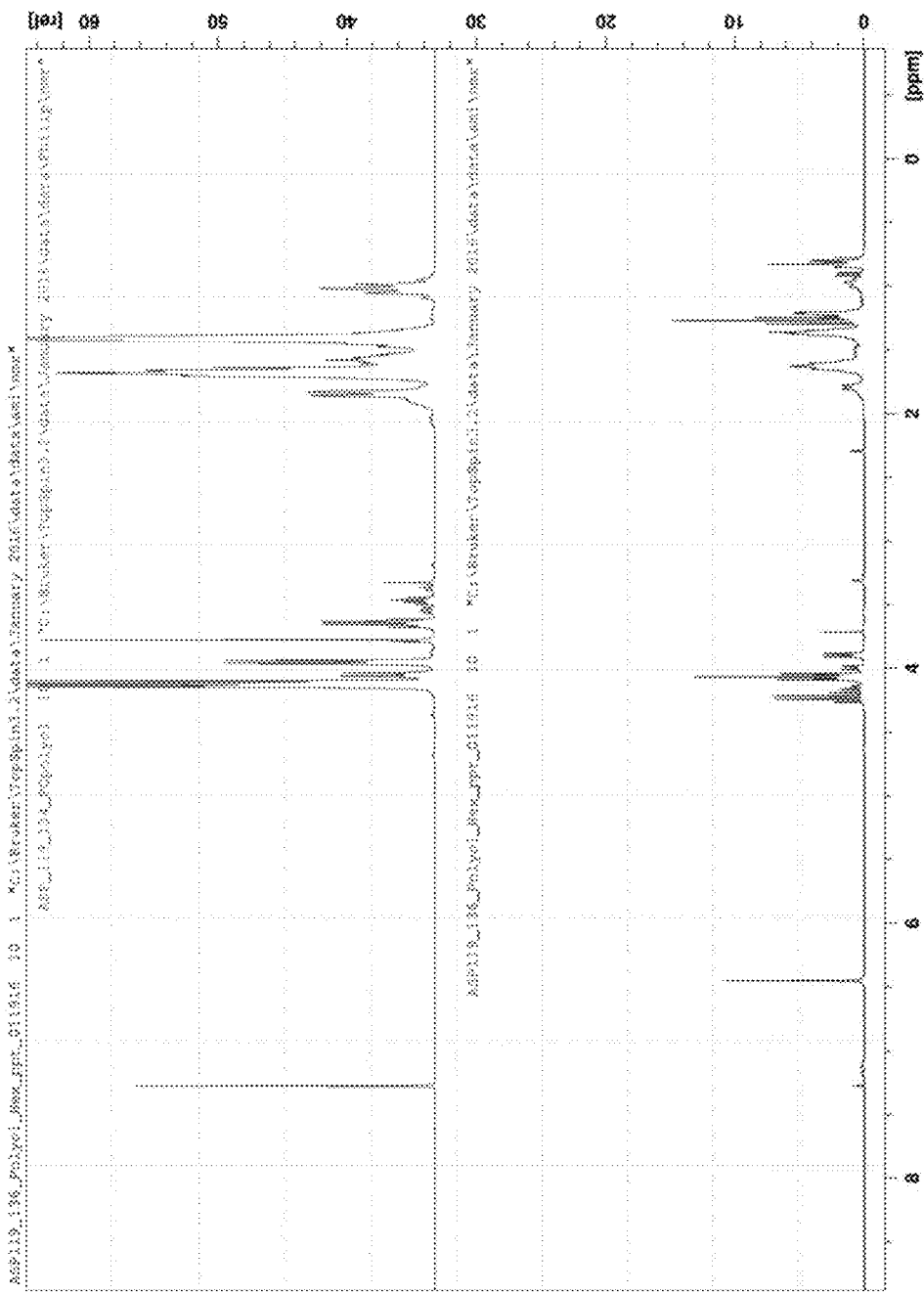
FIG. 3. H-NMR overlay of PC polyol (above) and transesterified polycarbonate polyol end capped with DEMM in excess DEMM (below). The disappearance/shift of the methylene protons from 3.6 ppm in the polyol after the reaction is indicative of near complete

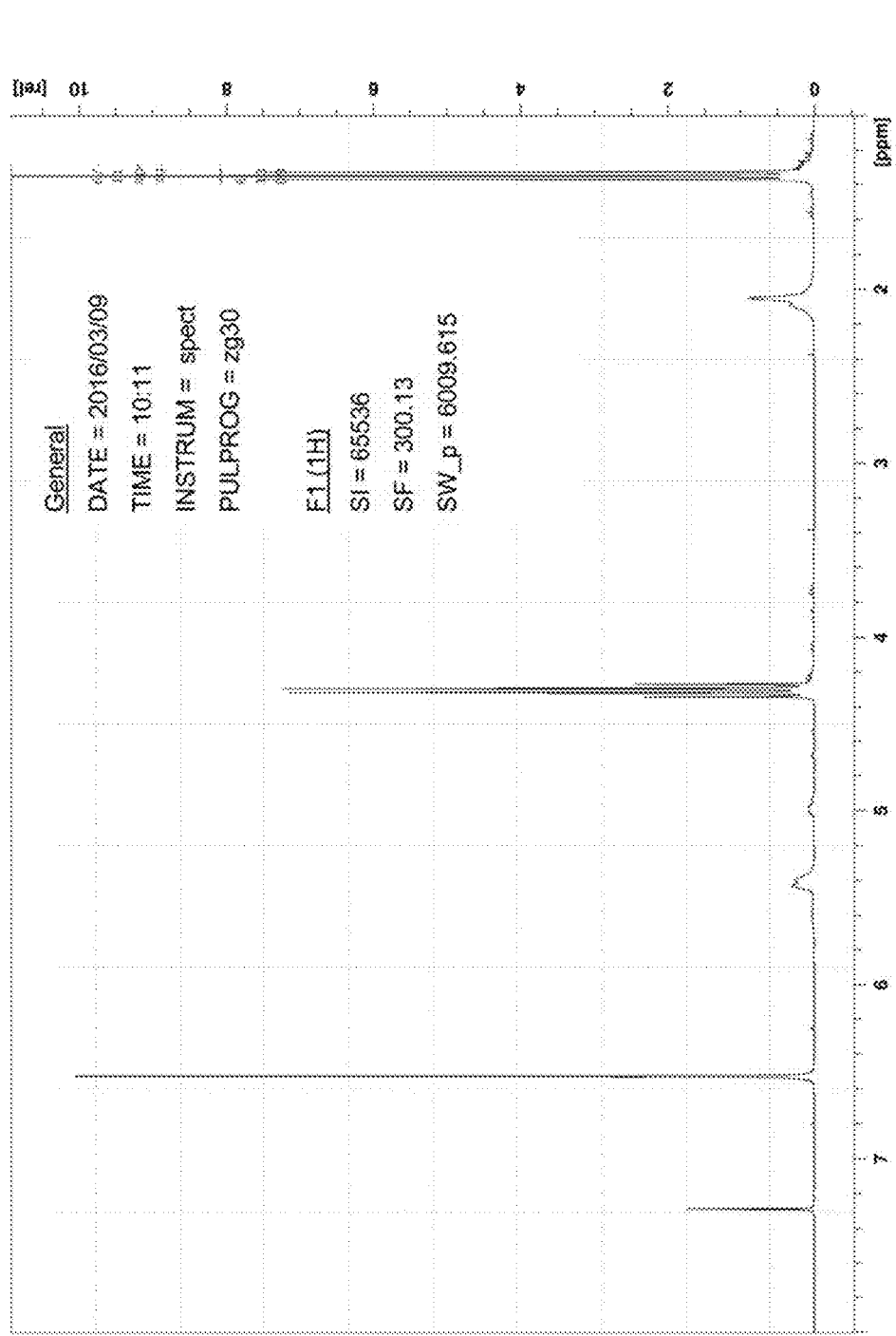
FIG. 4A: Full scale H-NMR of end capped polybutadiene in excess DEMM. Confirmation of transesterification can be observed by the absence of peaks at 4.1 ppm corresponding to the methylene groups attached to the OH functionality in the polyol.

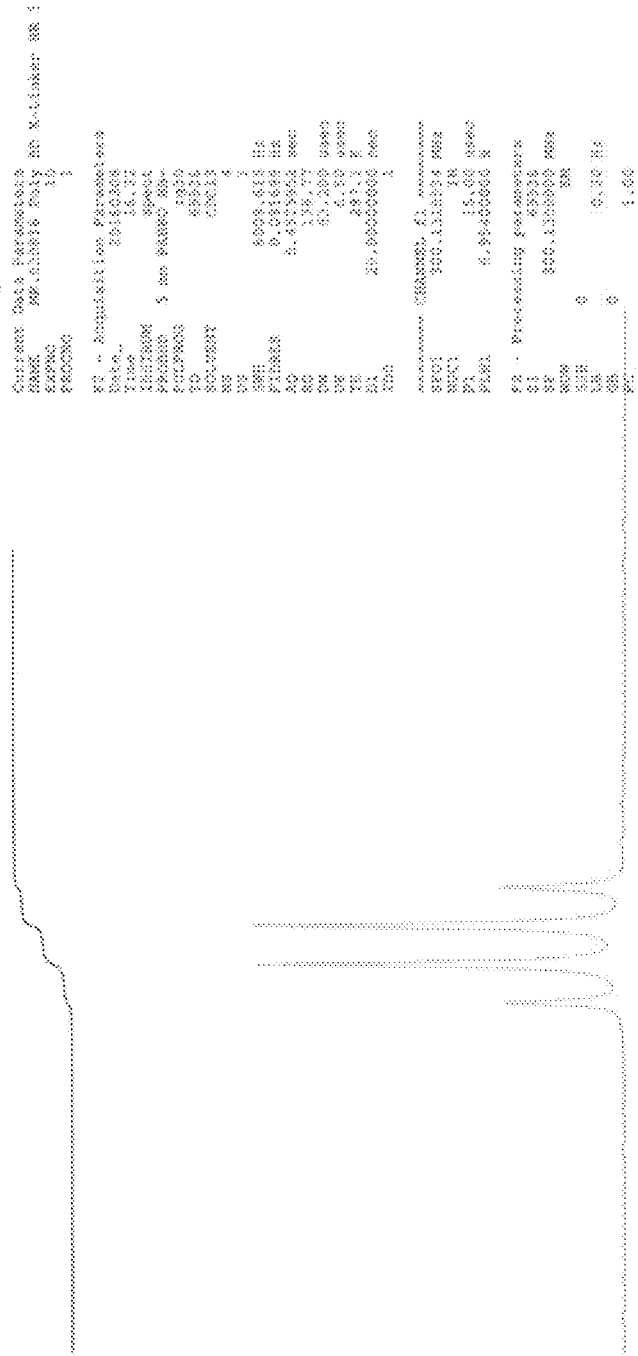
FIG. 4B: Zoomed section of H NMR spectrum from 4A above showing the consumption of the methylene protons that appear at 4.1 ppm

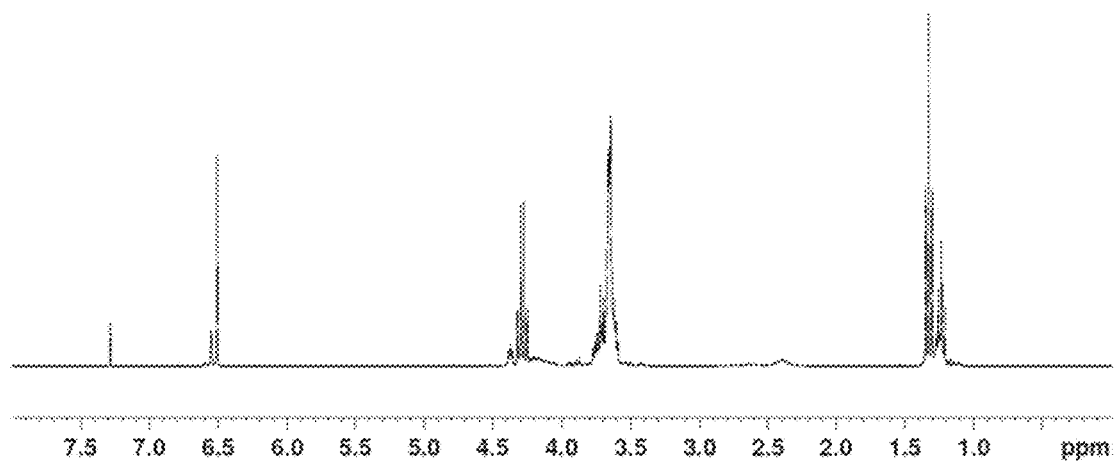
FIG. 5A: Full scale H-NMR of transesterification of DEMM with PEG 300. Formation of new species can be confirmed in the 6.5 ppm methylene (double bond) region.
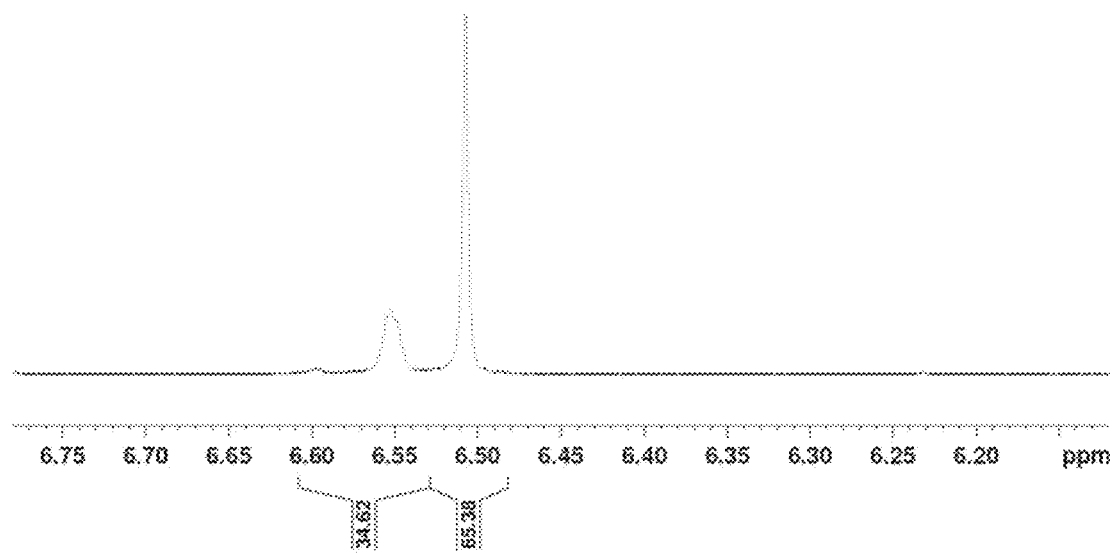
FIG. 5B: Integration of the two species seen in the 6.5 ppm region of the spectrum in 5A confirms the amount of transesterified species is about 35% (with about 65 wt.% residual DEMM).

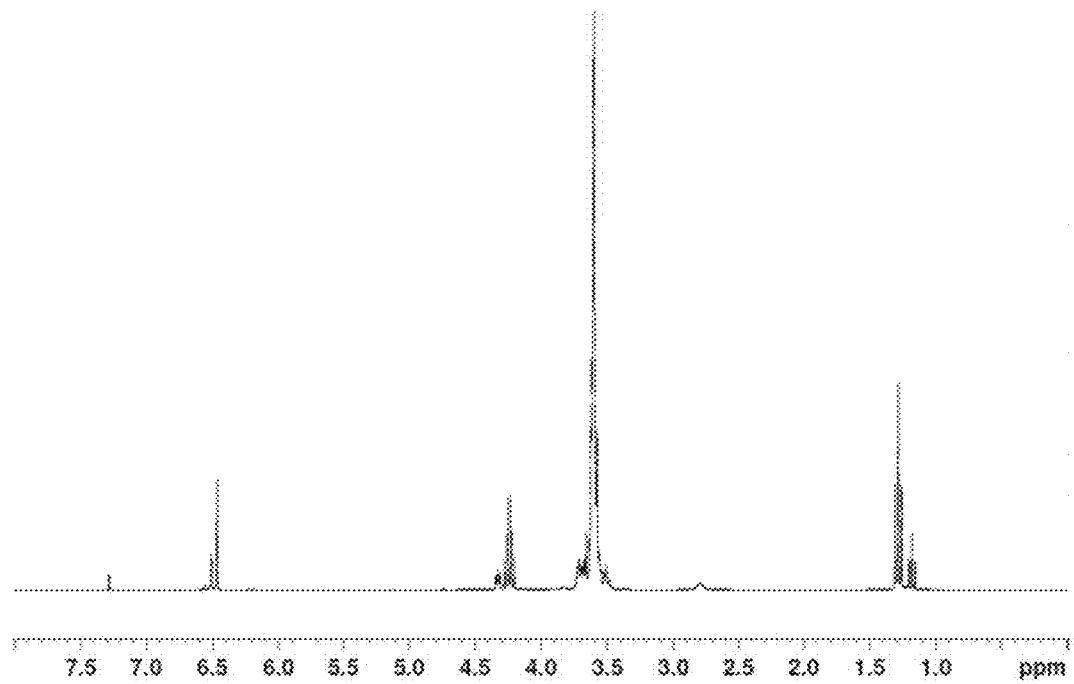
FIG. 6A: Full scale H-NMR of transesterification of DEMM with glycerol ethoxylate. Formation of new species can be confirmed in the 6.5 ppm methylene (double bond) region.
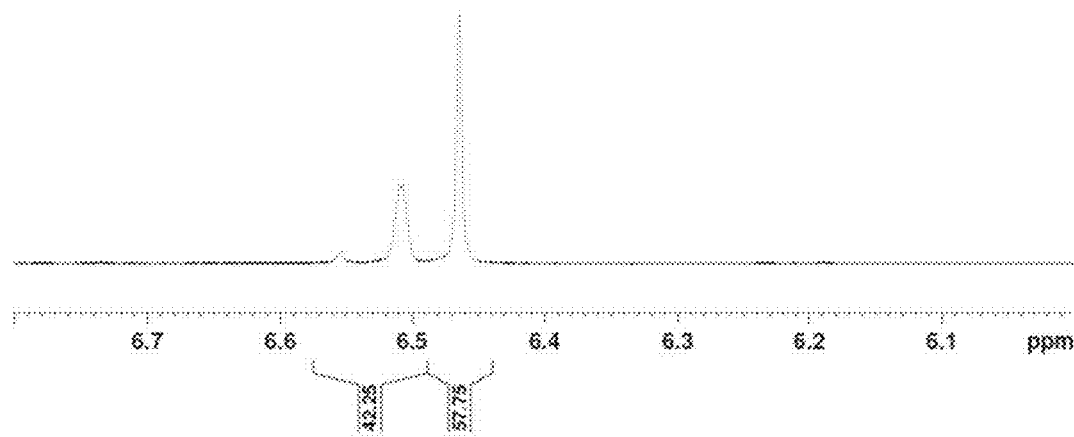
FIG. 6B. Integration of the two species seen in the 6.5 ppm region of the spectrum in 6A above confirms the amount of transesterified species is around 42% (with 58% residual DEMM).

POLYMER AND OTHER COMPOUNDS FUNCTIONALIZED WITH TERMINAL 1,1-DISUBSTITUTED ALKENE MONOMER(S) AND METHODS THEREOF

RELATED APPLICATIONS

This application claims priority to U.S. Provisional Patent Applications Ser. No. 62/421,754 filed on Nov. 14, 2016 by Palsule et al. and 62/345,334 filed on Jun. 3, 2016 by Palsule et al. and to U.S. patent application Ser. No. 15/437,164 filed on Feb. 20, 2017 by Palsule et al., now U.S. Pat. No. 9,745,164 and Ser. No. 15/234,191 filed on Aug. 11, 2016 by Palsule et al., now U.S. Pat. No. 9,617,377, the contents of which are each incorporated herein by reference in its entirety.

FIELD

Disclosed are novel compounds and compositions containing polymers functionalized with one or more molecules having an alkenyl group. Further disclosed are methods for the preparation of the novel compounds and compositions, as well as cross-linked polymers and block copolymers including the novel compounds. The molecule(s) having an alkenyl group preferably is a 1,1-diester-1-alkene compound. Preferably the polymer includes a plurality of spaced apart alkenyl groups. For example, the polymer may have a central polymer portion and the molecules having an alkenyl group are attached to one or more ends of central polymer portion. Preferred central polymer portions include, consist essentially of, or consist entirely of one or more polyols.

BACKGROUND

Polymers such as polyesters, polycarbonates, and other polyols, are generally linear or branched molecules that typically do not have unsaturated functional groups, such as alkenyl groups.

1,1-diester-1-alkenes, such as methylene malonates, contain two diester groups, and an alkylene group disposed between the two diester groups. Recent developments in synthesis of these compounds facilitate the synthesis of these compounds and their use in a variety of applications, see Malofsky U.S. Pat. No. 8,609,885; U.S. Pat. No. 8,884,051; and U.S. Pat. No. 9,108,914; incorporated herein by reference in their entireties for all purposes. Processes for transesterifying these compounds have also been recently developed. Malofsky et al. WO 2013/059473, US 2014/0329980, incorporated herein by reference in their entirety for all purposes, discloses the preparation of multifunctional methylene malonates by multiple synthetic schemes. One disclosed process involves reacting a methylene malonate with a polyol in the presence of a catalyst to prepare compounds wherein one of the ester groups on the methylene malonates undergoes transesterification to react with the polyol and form multifunctional compounds (multifunctional meaning the presence of more than one methylene malonate core unit). The use of enzyme catalysis is disclosed. Sullivan, U.S. Ser. No. 14/814,961 filed Jul. 31, 2015 discloses transesterification of 1,1-disubstituted-1-alkenes using certain acid catalysts, incorporated herein by reference in its entirety for all purposes.

What is needed are compositions useful in preparing polyesters which can be crosslinked elegantly without the need for problematic catalysts and use relatively mild conditions. Coatings prepared from such compositions that exhibit enhanced properties are needed, such enhanced properties include flexibility, adhesion to substrates, pencil hardness, solvent resistance, abrasion resistance, ultraviolet ray resistance, high temperature resistance, and the like. Processes that prepare the components for such coating and the coatings are needed.

SUMMARY

One aspect of the invention is directed at a functionalized polyhydric compound comprising a central portion (preferably an isocyanurate trimer or a central polymer portion); and two or more residues of 1,1-disubstituted alkene compound(s) wherein one or both of the disubstituted groups include an ester group; wherein each of the residues of the 1,1-disubstituted 1-alkene compound(s) is attached to a different end of the central portion; so that the functionalized polymer has at least two spaced apart alkene functional group. The central portion preferably is formed from a polyhydric compound. The central portion may be an isocyanurate trimer and the 1,1-disubstituted alkene compounds may be spaced apart by the isocyanurate trimer. The central portion may include two or more ends that are spaced apart by five or more atoms, wherein each of the residues of the 1,1-disubstituted 1-alkene compounds(s) is attached to a different end of the central portion.

The addition of an alkenyl group to a central polymer portion to form a functionalized polymer provides a new site for reacting the central polymer with other molecules. For example, an alkenyl group may be used to graft the central polymer portion to another polymer. As another example, a plurality of spaced apart alkenyl groups may be attached to the central polymer portion to form a multi-block structure, such as a network structure in which the central polymer portion is connected to multiple blocks of a second polymer portion. The alkenyl group(s) may copolymerize during a polymerization of an alkenyl containing monomer. Such a polymerization may be a free radical polymerization, an anionic polymerization, or a cationic polymerization. An anionic polymerization may include one or more of the features described in International Patent Application PCT/US15/48846 (by Sullivan et al., filed on Sep. 8, 2015 and published on Mar. 17, 2016 as WO 2016/040261 A1), US Patent Application Publication 2016/0068616A (by Palsule et al. and published on Mar. 10, 2016) and U.S. Pat. No. 9,249,265 B1 (by Stevenson et al. and issued on Feb. 2, 2016), each incorporated by reference in its entirety. As another example, the functionalized polymer may be cross-linked using a cross-linking compound (e.g., a sulfur cross-linking compound or a non-sulfur cross-linking compound) and/or a cross-linking coagent capable of forming a bridge between two or more alkenyl groups.

The central polymer portion may include, consists essentially of or consist entirely of one or more polyols. The one or more polyols may be one or more polyether polyols, polysiloxane polyols, polycarbonate polyols, polyester polyols, polyethylene glycol, acrylic polyol or polybutadiene polyols. The one or more polyols may be a linear chain having two chain ends or may be a branched chain having 3 or more chain ends. Preferably one or more, two or more, or all of the chain ends may have hydroxyl groups capable of reacting with an ester group. Hydroxyl groups may also be pendent on the main chain of the polyol. For example, a functional compound may include an ester group and may be attached to the polyol by a transesterification reaction. Examples of transesterification reactions include those disclosed in US Patent Application Publication US 2016/

0221922 A1 (by Sullivan et al., published on Aug. 4, 2016) and U.S. patent application Ser. No. 15/234,191 (by Palsule et al. and filed on Aug. 11, 2016), both incorporated herein by reference in their entirety. The polyol may include, one or more, two or more, or three or more hydroxyl groups.

The functionalized polymers disclosed herein may be fabricated into films or coatings. The coating or film may have a thickness of about 0.001 µm or more, about 0.1 µm or more, about 1 µm or more, or about 2 µm or more. The coating or film preferably has a thickness of about 200 µm or less, more preferably about 50 µm or less, and most preferably about 20 µm or less.

The functional compound having an alkenyl group may be a 1,1-disubstituted alkene compound. 1,1-disubstituted alkene compounds include the monomers described in US Patent Application Publication US 2016/0068616 A1 (for example, see paragraphs 0022, and 0030-0045), incorporated herein by reference. Such a functional compound may have a single alkenyl group, or may be multifunctional (having two or more alkenyl groups). Multifunctional compounds having a plurality of alkenyl groups includes those described in US Patent Application Publication US 2016/0068616 A1 (see e.g., paragraph 0042), incorporated herein by reference. Preferably some or all of the 1,1-disubstituted alkene compounds have a single alkenyl group.

The functionalized polymer may be in a solvent.

The functionalized polymer may be concentrated (e.g., substantially or entirely free of a solvent). In a concentrated system, the amount of any solvent preferably is about 10 weight percent or less, about 5 weight percent or less, about 2 weight percent or less, or about 1 weight percent or less. The amount of solvent may be about 0 weight percent or more, or about 0.1 weight percent or more.

Disclosed is a polymerizable composition including i) a functionalized polymer having one or more alkenyl groups and ii) one or more monomers capable of polymerizing with the alkenyl group of the functionalized polymer. Preferably, the one or more monomers includes, consists essentially of, or consists entirely of one or more 1,1-diester-1-alkenes.

Disclosed is a cross-linked network including polymer blocks of a first polymer connected by a second block including or consisting entirely of one or more 1,1-diester-1-alkenes. The first polymer block preferably is a polyol (such as the polyol of a central polymer portion as discussed herein).

Disclosed is a functionalized polyhydric compound comprising a central portion of a polymeric polyol having two or more ends, wherein one or more of the ends is capped with a reside of a 1,1-disubstituted alkene compound, wherein the functionalized polyhydric compound is a functionalized polymer.

Disclosed is a method of forming a functionalized polyhydric compound in a continuous reaction (e.g., using a tubular reactor) by reacting a 1,1-disubstituted 1-alkene compound and a polyol polymer including a step of transesterification. Preferably the tubular reactor is packed with or otherwise includes one or more catalysts.

Disclosed is a functionalized polyhydric compound comprising: a central polymer portion having two or more ends that are spaced apart by a plurality of monomers units including adjacent monomers units that are covalently bonded; wherein the central polymer portion is a homopolymer consisting essentially of monomer units that are identical, or a copolymer having monomer units including a first monomer and one or more comonomers different from the first monomer; wherein the monomers units of the central polymer portion include a terminal monomer unit at each of the ends of the central polymer portion; and one or more residues of 1,1-disubstituted alkene compound(s) wherein one or both of the disubstituted groups includes an ester group; wherein each of the residues of the 1,1-disubstituted 1-alkene compound(s) is attached to a different end of the central polymer portion (i.e., to different terminal monomer units of the central polymer portion) or pendent to the central polymer portion; so that the functionalized polymer has at least one alkene functionality. Preferably the functionalized polyhydric compound is a functionalized polymer (preferably having 4 or more monomer units).

Disclosed is a method of cross-linking a polyol using monomeric 1,1-diester-1-alkenes.

Disclosed is a grafted polymer including, or consisting essentially of one or more 1,1-diester-1-alkenes, and including one or more grafts. The grafts may be a polyol. Preferred grafts include a polyester, a polyether, a polybutadiene, a polycarbonate, polyethylene glycol, an acrylic containing polymer, or a siloxane-containing polymer.

Disclosed is a method of grafting a polyol to a polymer including one or more 1,1-diester-1-alkene monomers. Preferably the grafting occurs during the polymerization of the monomer. For example, the grafting may occur during the copolymerization of an alkenyl group attached to the polyol.

Disclosed is an article including a coating formed by reacting one or more polymerizable monomers with a functionalized polymer having a polyol backbone and one, two or more terminal 1,1-disubstituted alkenes. The polymerizable monomer preferably includes, consists essentially of, or consists entirely of one or more 1,1-disubstituted alkenes. More preferably, the polymerizable monomer includes one or more methylene malonates. The concentration of the one or more polymerizable monomers may be about 1 weight percent or more, more preferably about 10 weight percent or more, and most preferably about 28 weigh percent or more. The amount of the one or more polymerizable monomers may be about 98 weight percent or less, preferably about 90 weight percent or less, and most preferably about 80 weight percent or less. The coating may be attached to any substrate. For example, the substrate may be a metallic substrate, a polymer substrate, a fiber substrate, a glass substrate, or a ceramic substrate.

BRIEF DESCRIPTION OF DRAWINGS

FIG. 1C illustrates typical NMR acquisition parameters.

FIG. 2 is an illustrative Thermogravimetric Analysis (TGA) curve of DEMM crosslinked with end capped aliphatic polyester polyol. The aliphatic polyester polyol may be end capped with a residue of DEMM.

FIG. 3 is an illustrative proton NMR overlay of polycarbonate polyol (top) and transesterified polycarbonate polyol end capped with DEMM in excess DEMM (bottom). The disappearance/shift of the methylene protons from 3.6 ppm in the polyol after the reaction is indicative of near complete transesterification FIG. 4A is an illustrative full scale proton NMR of end capped (e.g., with a residue of DEMM) polybutadiene in excess DEMM. Confirmation of transesterification can be observed by the absence of peaks at 4.1 ppm corresponding to the methylene groups attached to the OH functionality in the polyol.

FIG. 4B is an illustrative enlarged section of the proton NMR spectrum from 4A above showing the consumption of the methylene protons that appear at 4.1 ppm.

FIG. 5A: is an illustrative full scale proton NMR of transesterification of DEMM with polyethylene glycol PEG 300. Formation of new species can be confirmed in the 6.5 ppm methylene (double bond) region.

FIG. 5B is an illustrative proton NMR spectrogram of an end-capped polyethylene glycol PEG 300 polyol showing two species in the 6.5 ppm region of the spectrum in 5A. The amount of the transesterified species is around 35 percent and the amount of unreacted DEMM is about 65 percent.

FIG. 6A is an illustrative proton NMR spectrogram of transesterification of DEMM with glycerol ethoxylate. Formation of new species can be confirmed in the 6.5 ppm methylene (double bond) region.

FIG. 6B is an illustrative proton NMR spectrum showing the integration of the two species seen in the 6.5 ppm region of the spectrum in FIG. 6A. The amount of transesterified species is around 42% and the amount of unreacted DEMM is about 58 percent.

DETAILED DESCRIPTION

Figure 1A:
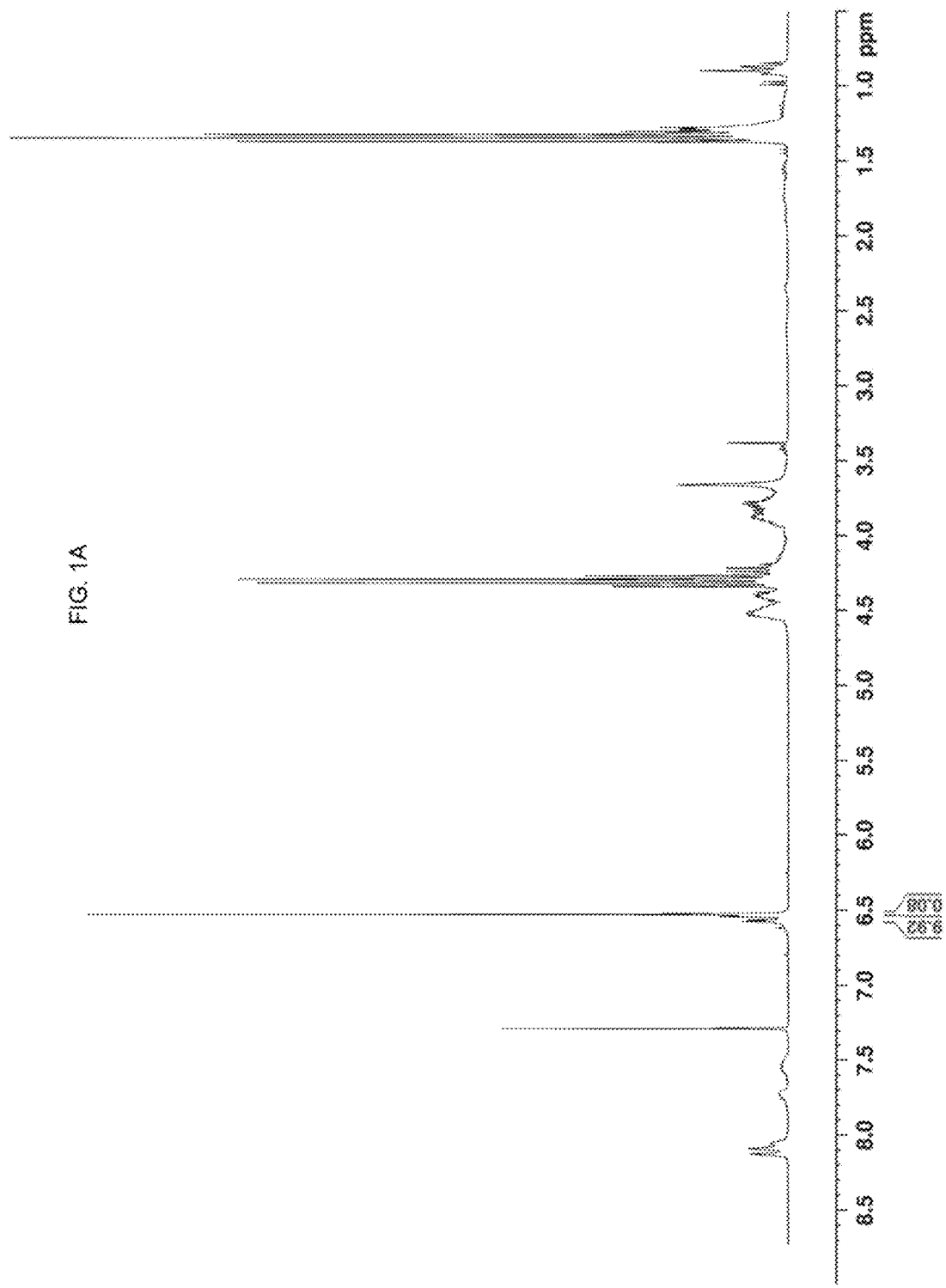
FIG. 1A is an illustrative proton NMR spectrogram of reaction mixture including DEMM and a terate polyol end capped with DEMM.

The explanations and illustrations presented herein are intended to acquaint others skilled in the art with the invention, its principles, and its practical application. Those skilled in the art may adapt and apply the invention in its numerous forms, as may be best suited to the requirements of a particular use. Accordingly, the specific embodiments of the present invention as set forth are not intended as being exhaustive or limiting of the teachings. The scope of the teachings should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. Other combinations are also possible as will be gleaned from the following claims, which are also hereby incorporated by reference into this written description.

Unless defined otherwise, all technical and scientific terms used herein have the meaning commonly understood by a person skilled in the art to which this disclosure belongs. The following references provide one of skill with a general definition of many of the terms used in this disclosure: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991).

Acid catalyst, as used herein, is an acidic species that catalyzes the transesterification reaction while minimizing or not contributing to side reactions. One or more as used herein means that at least one, or more than one, of the recited components may be used as disclosed. Nominal as used with respect to functionality refers to the theoretical functionality; generally, this can be calculated from the stoichiometry of the ingredients used. Heteroatom refer to atoms that are not carbon or hydrogen such as nitrogen, oxygen, sulfur, and phosphorus; heteroatoms may include nitrogen and oxygen. Hydrocarbyl, as used herein, refers to a group containing one or more carbon atom backbones and hydrogen atoms, which may optionally contain one or more heteroatoms. Where the hydrocarbyl group contains heteroatoms, the heteroatoms may form one or more functional groups well-known to one skilled in the art. Hydrocarbyl groups may contain cycloaliphatic, aliphatic, aromatic, or any combination of such segments. The aliphatic segments can be straight or branched. The aliphatic and cycloaliphatic segments may include one or more double and/or triple bonds. Included in hydrocarbyl groups are alkyl, alkenyl, alkynyl, aryl, cycloalkyl, cycloalkenyl, alkaryl, and aralkyl groups. Cycloaliphatic groups may contain both cyclic portions and noncyclic portions. Hydrocarbylene means a hydrocarbyl group or any of the described subsets having more than one valence, such as alkylene, alkenylene, alkynylene, arylene, cycloalkylene, cycloalkenylene, alkarylene and aralkylene. As used herein percent by weight or parts by weight refer to, or are based on, the weight or the compounds or compositions described unless otherwise specified. Unless otherwise stated parts by weight are based 100 parts of the relevant composition.

The functionalized polyhydric compound includes a central portion formed from a polyhydric compound wherein one or more of the hydroxyl groups are reacted with a functional compound to functionalize the polyhydric compound. The polyhydric compound may be a monomeric compound having two or more hydroxyl groups, or may be a polymeric compound including two or more hydroxyl groups. The functionalized polyhydric compound preferably includes functional groups different from the structure along the length of the central portion. Preferably, the functionalized polyhydric compound includes an alkenyl group. For example, the functional compound may be a 1,1-disubstituted-1-alkene. The central portion generally has two or more ends. At least one of the ends of the central portion preferably is attached to a functional compound. Preferably two or more, or all of the ends of the central portion are attached to the central compound. It will be appreciated that when a hydroxyl group reacts with a functional compound, a residue of the polyhydric compound is attached to the functionalized compound.

When the polyhydric compound is a polymer, the central portion is a central polymer portion.

The functionalized polymer includes a central polymer portion having two or more ends. At least one of the ends of the central polymer portion is attached to a functional compound having one or more functional groups. The functional compound preferably includes functional groups different from the structure along the length of the central polymer portion. Preferably, the functional compound includes an alkenyl group. For example, the functional compound may be a 1,1-disubstituted-1-alkene.

The functionalized polyhydric compound (e.g., the functionalized polymer) preferably includes two or more alkenyl groups. Preferably the two or more alkenyl groups includes a first alkenyl group that is spaced apart from a second alkenyl group. For example, the alkenyl groups may be located primarily on the terminal compounds (e.g., terminal monomers) of the functionalized polymer.

The functionalized polyhydric compound (e.g., the functionalized polymer) may be prepared by the reaction of a polyhydric compound (e.g., a polyol) having a terminal or pendent hydroxyl group with a 1,1-disubstituted alkene. For example, the reaction may include a transesterification reaction. The reaction may cap one or more, two or more, or all of the terminal ends of the polyhydric compound (e.g., the polyol) with 1,1-disubstitued alkene compounds.

The polyhydric compound preferably is sufficiently long so that the hydroxyl groups can each readily react with a functional compound according to the teachings herein. For example, the oxygen atoms of the hydroxyl group may be spaced apart by about 5 or more additional atoms, more preferably about 7 or more additional atoms, and more preferably about 9 or more additional atoms.

In various aspects, the polyhydric compound may provide a mechanical or physical characteristic (e.g. flexibility, low temperature impact resistance, ductility, or any combination thereof) requiring that the polyhydric compound be present as an oligomeric compound or a polymer. As such, the spacing between hydroxyl groups on the polyhydric compound may be about 12 or more, about 20 or more, about 50 or more, or about 100 or more.

The polyhydric compound preferably is sufficiently short so that the polyhydric compound has a large concentration of functional groups. For example, the ratio of the weight average molecular weight to the number of terminal hydroxyl groups per molecule (e.g., per polymer molecule) is about 200,000 or less, more preferably about 100,000 or less, even more preferably about 40,000 or less, even more preferably about 10,000 or less, and most preferably about 4,000 or less.

Monomeric Polyhydric Compounds

The polyhydric compound may be a monomeric compound having two or more spaced apart hydroxyl groups. The monomeric polyhydric compound may be a linear compound or a branched compound.

Examples of branched polyhydric compounds include neopentyl glycol, pentaerythritol, methyl-substituted propanediols, ethyl-substituted propanediols, methyl-, ethyl-, propyl-substituted butanediols, methyl-, dimethyl-, trimethyl-, ethyl-, diethyl-, triethyl-, propyl-, dipropyl-substituted hexanediols, etc. For example, the branched polyhydric compound include 2-methyl-1,3-propane diol, 3-methyl-I,5-pentane diol, neopentyl glycol, 2,2-diethyl-1,3-propanediol, 2-butyl-2-ethyl-1,3-propane diol, 2,2-diethyl-1,3-propanediol, 2-butyl-2-ethyl-1,3-propane diol, 2-methyl-1,8-octanediol, 2,2,4-trimethyl-I,3-pentane diol, 2-ethyl-1,3-hexanediol, 1,4-cyclohexane dimethanol, or any combination thereof. Other examples of branched polyhydric compounds will be apparent to the person of ordinary skill in the art.

Linear polyhydric compounds include hydrocarbyl chains which are free of branching. Examples of such compounds include 1,5-pentanediol, 1,6-hexanediol, 1,7-heptanediol, 1,8-octanediol, 1,9-nonanediol, 1,10-decanediol, 1,12-dodecanediol, 1,13-tridecanediol, diethylene glycol, triethylene glycol, tetraethylene glycol, 1,4-cyclohexanedimethanol, 1,5-decalindiol, etc. Preferred straight chain polyhydric alcohols are 1,6-hexanediol, 1,8-octanediol, 1,10-decanediol, 1,12-dodecanediol, tetraethylene glycol, and mixtures thereof.

Additional examples of polyhydric compounds include compounds having one or more nitrogen atoms. Preferred polyhydric compounds including a nitrogen atom include one or more cyanurate groups, such as an isocyanurate group. The polyhydric compound include a tris(hydroxyalkyl) isocyanurate, a tris(hydroxybenyzl)cyanurate. For example, the polyhydric compound may include 1,3,5-tris(2-hydroxyethyl)isocyanurate.

Central Polymer Portion

The central polymer portion may be a homopolymer consisting substantially of or entirely of one monomer compound, or a copolymer including two or more different monomers compounds. Examples of copolymers include alternating copolymers, random copolymers and block copolymers.

The central polymer portion preferably has a repeat unit consisting of 1 or 2 monomers.

The central polymer portion preferably includes, consists substantially of, or consists entirely of one or more polyols. Any polyol may be used provided that the polyol includes one or more, or two or more hydroxyl groups at the end of the polymer chain or along the length of the polymer chain. Preferred polyols include polyesters, polyethers, polybutadiene polyols, polycarbonates, polyacrylates (e.g., including acrylic acid and/or methacrylic acid).

The central polymer portion may have a backbone, which is defined by the covalently bonded atoms required to connect the ends of the central polymer portion. The atoms of the backbone generally exclude pendant groups unless they link to an additional monomer unit, such as in a polymer having long chain branching with 2 or more monomer units.

As used herein, a monomer compound refers to the chemical structure of the molecule, and a monomer unit refers to the individual molecule. For example, a first monomer unit and a second monomer may refer to molecules having the same or different chemical structures. Similarly, a first monomer compound and a second monomer compound refers to molecules having different chemical structures.

An alternating comonomer may consist essentially of a first monomer compound (e.g., R1–$M^1$–R2) and a second monomer compound (e.g., R3–$M^2$–R4) in an alternating arrangement. Here, the central polymer portion ($P^1$) may be described as including or consisting essentially of a repeat unit (e.g., A) that is formed by one first monomer compound and one second monomer compound:

$$P^1 = R1-(A)_n-R4,$$

where A=–$M^1$–$M^2$–n is at least 3, and at least one of R1 and R4 is capable of reacting with the functionalized compound to add a functional group (preferably at least an alkenyl group) to the end of the central polymer portion. R1 or R4 preferably undergo transesterification and more preferably, R1 and R4 both undergo transesterification.

The first monomer may be a terminal monomer on two ends of the central polymer portion ($P^2$):

$$P^2 = R1-(A)_n-M^1-R2,$$

where A=–$M^1$–$M^2$–n is at least 3, and at least one of R1 and R2 is capable of reacting with the functionalized compound to add a functional group (preferably at least an alkenyl group) to the end of the central polymer portion. R1 or R2 preferably undergo transesterification and more preferably both R1 and R2 undergo transesterification.

The repeat units of the central polymer portion may have the same chemical structure or may have two or more different chemical structures.

A monomer compound or a repeat unit of the central polymer portion may include aliphatic groups, aromatic groups, or both. Aromatic groups may be on the backbone or may be present as a pendant group. Aliphatic groups may be on the backbone or may be present as a pendant group.

The central polymer portion may be formed from one or more monomers using a condensation reaction (e.g., a polycondensation reaction). For example, the condensation may be a reaction between an alcohol group of a first monomer unit and an acid group of a second monomer unit (e.g., a carboxyl group, —CO(OH)) in which an ester linkage is formed to join the two monomer units.

The central polymer portion may include ester linkages attaching adjacent repeat units, the central polymer portion may include ester linkages attaching monomer units of a repeat unit, or both.

A central polymer portion may be formed from at least a monomer compound: (HO-$M^3$-O(OH)C, having an alcohol group and a carboxylic acid group, so that the central polymer portion includes the repeating unit: $M^3$. The central polymer portion may include, consists essentially of, or consist entirely of the repeating unit $M^3$.

A central polymer portion may be formed from a ring opening polymerization of one or more monomer compounds.

A central polymer portion may be formed from a polycondensation reaction of at least a first monomer compound that is a diol and a second monomer compound that is a diacid. All of the diols may be the same or there may be two or more different monomer compounds that are diols. All of the diacids may be the same or there may be two or more different monomer compounds that are diacids. The polycondensation reaction preferably results in the generation of water molecules. The central polymer portion may be produced with an excess of diol so that each end of the central polymer portion has a hydroxyl group. Preferably each end of the central polymer portion has a hydroxyl group. More preferably, each end of the central polymer portion has a hydroxyl group (e.g., on a terminal monomer unit). Preferably the hydroxyl groups reacts with a functionalized compound to form an ester linkage.

Preferably, the functionalized polymer includes one or more functional compounds (Z) each connected to an end of the central polymer portion (P) by an ester linkage, such as shown below for a central polymer portion having two ends:

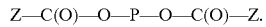

Z—C(O)—O—P—O—C(O)—Z.

Preferably the central polymer portion is saturated. Any alkenyl groups on the functionalized polymer preferably are only on one or more functional compounds that is each attached to a different end of the central polymer portion.

Polyol

The functionalized polymer preferably is formed by reacting a polyol (i.e., a compound having two or more functional hydroxyl groups (i.e., —OH groups) available for reaction. The hydroxyl groups are preferably available for an organic reaction. Preferably, the hydroxyl groups include or consist essentially of terminal or pendent hydroxyl groups.

The polyol may be monomeric, oligomeric, or polymeric.

Monomeric polyols are typically low molecular weight compounds having about 2 or more hydroxyl groups. Preferred monomeric polyols have a molecular weight of about 400 g/mole or less, more preferably about 300 g/mole or less and most preferably about 250 g/mole or less. Two or more hydroxyl groups of the monomeric diol preferably are sufficiently spaced apart so that they are not geminal diols and are not vacinal diols. Preferred monomeric polyols include glycerin, pentaerythritol, erythritol, ethylene glycol, sucrose, resorcinol, 1,4-butanediol, 1,6-hexanediol, propylene glycerol, bisphenol A, 4,4'-dihydroxydicyclohexyl, 1,4-pentanediol, 1,5-pentanediol, mannitol, sorbitan, 2,5-tetrahydrofuran-dimethanol, and 1,2,6-hexanetriol.

Polyester Polyol

The central polymer portion may include a polyester polyol, which may be a homopolymer or a copolymer. Examples of polyesters homopolymers and copolymers, monomers for preparing a polyester, and methods for preparing a polyester that may be employed for the central polymer portion include polymers described in U.S. Pat. No. 4,725,664 (see for example column 3 line 15 to column 6, line 41) by Halmess et al., U.S. Pat. No. 4,067,850 by Kohler et al., U.S. Pat. No. 2,973,339 by Muenster et al., U.S. Pat. No. 3,651,016 by Hrach et al, U.S. Pat. No. 4,377,682 by Ohguchi et al.; U.S. Pat. No. 3,972,852 by Inata et al.; U.S. Pat. No. 4,263,370 by Login et al., U.S. Pat. No. 5,700,882 by Jones et al., U.S. Pat. No. 9,309,345 by Hickey et al., and U.S. Pat. No. 8,318,893 by Hoshino et al. each incorporated herein by reference.

The polyester polyol may include one or more repeating units characteristic of the following polymers: a polyglycolide (i.e., poly(oxy(1-oxo-1,2-ethanediyl), such as from the condensation of glycolic acid); polylactic acid (e.g., from the ring opening of lactide), polycaprolactone (e.g., from the ring opening of caprolactone), a polycaprol, a polyhydroxyalkanoates (e.g., polyhydroxybutyrate), polyethylene adipate, PHBV (i.e., a copolymer of 3-hydroxybutanoic acid and 3-hydroxypentanoic acid, butyrolactone, and valerolactone), a polybutylene succinate (e.g., from the condensation of succinic acid and 1,4-butanediol), polyethylene terephthalate (e.g., from terephthalic acid and ethylene glycol), polybutylene terephthalate (e.g., from terephthalic acid and 1,4 butanediol), polytrimethylene terephthalate (PTT) (e.g., from the condensation of terephthalic acid and 1,3-propanediol), and polyethylene naphthalate (PEN) (e.g., from condensation of at least one naphthalene dicarboxylic acid with ethylene glycol). Another polyester that may be employed is a polymer formed from the condensation of 4-hydroxybenzoic acid 6-hydroxynaphthalene-2-carboxylic acid. The polyester may include an aliphatic dicarboxylic acid and/or an aliphatic diol.

The polyester may be an aromatic polyester. An aromatic polyester may be formed by reacting an aromatic acid component with a hydroxylated component.

The aromatic acid component of the aromatic polyester polyol composition can be, for example, phthalic acid based material, phthalic add, terephthalic acid, isophthalic acid, phthalic anhydride, pyromellitic anhydride, dimethyl terephthalate, polyethylene terephthalate, trimellitic anhydride, bottom residues, derivatives thereof, and combinations thereof. By phthalic acid based material as used herein is meant phthalic add or a derivative of phthalic acid. Examples of phthalic add based materials include, e.g., various phthalic adds such as terephthalic acid and isophthalic acid, phthalic anhydride, dimethyl terephthalate, polyethylene terephthalate, trimellitic anhydride, derivatives thereof, and combinations thereof. The phthalic acid based materials for use in preparing the polyester polyols can be (a) substantially pure phthalic acid or phthalic add derivatives, such as phthalic anhydride, terephthalic acid, dimethyl terephthalate, isophthalic add, and trimellitic anhydride; or (b) somewhat complex mixtures such as side stream, waste or scrap products containing residues of phthalic acid. In this context, "residues of phthalic acid" means any reacted or unreacted phthalic acid remaining in a product after its manufacture by a process in which phthalic acid or a derivative thereof is a starting component, including bottom residues. Complex mixtures of phthalic acid residues are further described in U.S. Pat. No. 5,922,779, which is herein incorporated by reference in its entirety.

A preferred phthalic acid based material for use in the preparation of the aromatic polyester polyols is phthalic anhydride. This component can be replaced by phthalic acid or a phthalic anhydride bottoms composition, a phthalic anhydride crude composition, or a phthalic anhydride light ends composition, as such compositions are defined in U.S. Pat. No. 4,529,744.

The aromatic acid component of the aromatic polyester polyol composition can comprise, for example, from about 20% to about 50% by weight of the aromatic polyester polyol composition, alternatively between about 20% to about 40% by weight.

The hydroxylated component of the aromatic polyester polyol composition of the present technology can be, for example, at least one aliphatic diol, at least one derivative thereof, or combinations thereof The hydroxylated component may be an aliphatic diol of generic formula

$$HO-R^1-OH \qquad (1):$$

where $R^1$ is a divalent radical selected from the group consisting of (a) alkylene radicals each containing from 2 through 6 carbon atoms, and (b) radicals of the formula

$$-(R^2O)_n-R^2- \qquad (2):$$

where $R^2$ is an alkylene radical containing from 2 through 3 carbon atoms, and n is an integer of from 1 through 3, and (c) mixtures thereof.

Examples of suitable aliphatic diols of formula (1) include ethylene glycol, propylene glycol, diethylene glycol, dipropylene glycol, trimethylene glycol, butylene glycols, 1,2-cyclohexanediol, poly (oxyalkylene) polyols each containing from two to four alkylene radicals derived by the condensation of ethylene oxide, propylene oxide, or any combination thereof, and the like. As those skilled in the art will appreciate, in the preparation of mixed poly(oxyethylene-oxypropylene) polyols, the ethylene and propylene oxides may be added to a starting hydroxyl-containing reactant either in admixture or sequentially. Mixtures of such diols can be employed, if desired. A presently most preferred aliphatic diol of formula (I) is diethylene glycol. Additionally, amine-based aliphatic hydroxylated materials (i.e., hydroxylated amines) may be utilized, such as for example, monoethanolamine, diethanolamine, and triethanolamine as long as all the amine functionality is completely consumed in the polyol.

Mixtures of diols can incorporate low molecular weight polyols (that is, compounds which contain less than 7 carbon atoms per molecule but which contain at least three hydroxyl groups per molecule) in an amount generally ranging from greater than 0 up to 100 percent of the total hydroxylated material. Such polyols comprise, for example, glycerol, 1,1,1-trimethylolpropane, 1,1,1-trimethylolethane, 2,2-dimethyl-1,3-propane diol, pentaerythritol, mixtures thereof, and the like.

The hydroxylated component of the aromatic polyester polyol composition can be, for example, diethylene glycol, glycerol, trimethylolpropane, pentaerythritol, ethylene glycol, propylene glycol, dipropylene glycol, trimethylene glycol, butylene glycols, 1,2-cyclohexanediol, hexane diols, pentane diols, poly oxyalkylene diols (e.g.—tri and tetra ethylene glycol), derivatives thereof, and combinations thereof.

The hydroxylated component of the aromatic polyester polyol composition can comprise, for example, from about 30% to about 80% based on the total weight of the aromatic polyester polyol composition. Alternatively, the hydroxylated component of the aromatic polyester polyol can be from about 30-65% by weight, based on the total weight of the polyester polyol. Alternatively, the hydroxylated material in the polyester polyol is from about 40-60% by weight, based on the total weight of the aromatic polyester polyol.

The polyesters may include one or more 1,4-arylene monomers such as terephthalic acid and hydroquinone, or a 2,6-arylene monomers such as 2,6-dihydroxynaphthalene, which are reacted with a linear and unbranched aliphatic diacid or diol whose functionality will be reactive with the functionality of the arylene monomer. The polyesters of the invention may be made by condensation of a diacid with diol by transesterification such as transesterification of hydroquinone diacetate or 2,6-naphthalene diacetate with an aliphatic diacid. The polyesters of the invention generally are made by the transesterification of a dialkyl terephthalate with straight chain, saturated aliphatic diols; the transesterification of hydroquinone diacetate with straight chain, saturated aliphatic diacids, direct esterification with straight chain saturated aliphatic diacids, esterification of terephthalyol chloride with straight chain, unbranched saturated diols, transesterification of 2,6-naphthalene diacetate with straight chain saturated unbranched diols and esterification using dicyclohexyl carbodiimide (DCC), diacid and diol as previously described. The alkyl is a lower alkyl having four or less carbons. In the latter reactions, any acid halide may be used in lieu of an acid chloride and propionate or butyrate (lower alkyls having four or less carbons) may be used in lieu of acetate. In this aspect of the invention, the polyesters may be defined as the reaction product of the a polymeric vehicle wherein the polyester is the reaction product of an arylene monomer selected from the group consisting hydroquinone, 2,6-hydroxynaphthalene, and mixtures thereof and a straight chain saturated aliphatic diol or diacid having 6 to 17 carbon atoms which diol or diacid is reactive with the arylene monomer and wherein R=alkyl having 1 to 4 carbon atoms or H, R'=alkyl having 1 to 4 carbon atoms and X=halogen.

The polyesters polyol may regularly alternate between aromatic substituents and straight chain unbranched substituents which separate or space the arylene groups. As the spacing between arylene groups increases to increase overall molecular weight, the lower number of repeating units enhances the liquid crystalline like properties of the polyesters which generally will have a number average molecular weight in the range of from about 350 to about 4,000 and preferably from about 400 to about 1800. The degree of polymerization may be controlled by the relative proportions of monomers in the reaction.

The polyhydroxy component may be selected for production of a polyester polyol based upon the desired properties of the polyol composition. Any suitable polyhydroxy compound can be used; for example, the polyhydroxy compound can be a dihydroxy compound (dial), trihydroxy compound (trial) a tetrahydroxy compound (tetraol), or a higher polyhydroxy compound. More specifically, the polyhydroxy compound can be ethylene glycol, diethylene glycol, polyethylene glycol, propylene glycol, dipropylene glycol, poly-propylene glycol, butanediol, pentanediol, hexanediol, glycerin, trimethylolpropane, pentaerythritol, or sorbitol, or a combination thereof.

A polycarboxylic acid can be a: diacid, triacid, or higher-functionality polycarboxylic acid or corresponding ester or anhydride including but not limited to polyfunctional aromatic adds, polyfunctional aromatic anhydrides, and polyfunctional aromatic esters (e.g., a diol monoester), and polyfunctional aliphatic adds, anhydrides, and polyfunctional esters thereof such as succinic acid, glutaric acid, adipic acid, phthalic acid, terephthalic acid, sebacic acid, azelaic acid, dodecanedioic acid, citric add, succinic anhydride, phthalic anhydride, dimethyl succinate, dimethyl glutarate, dimethyl adipate, dimethyl terephthalate and a combination thereof.

A hydrophobic material can be a plant oil (i.e., a plant-derived oil), or a fatty acid or ester derived therefrom; an animal oil (i.e., an animal-derived oil), or a fatty acid or ester derived therefrom; or a synthetic oil, synthetic fatty add, or synthetic fatty ester. By an oil is meant a hydrophobic compound regardless of its physical state at room temperature; i.e., an oil can be a solid, such as a solid fat, at room temperature.

The polyester polyol may include a polyfunctional aromatic acid, or an anhydride thereof, or an activated ester thereof, or a polyfunctional ester thereof, or a mixture thereof. For example, the polyester polyol may include the terephthalic acid, isophthalic acid, orthophthalic acid, trimellitic acid, pyromellitic acid, or any combination thereof.

Polycarbonate Polyol

The central polymer portion may be formed from a polycarbonate polyol. The polycarbonate polyol may be any polymer including, consisting essentially of, or consisting entirely of repeat units having a carbonate group (i.e., —O—C(=O)—O—). The polycarbonate polyol includes two or more hydroxyl groups (e.g., two or more terminal hydroxyl groups). The polycarbonate polyol may include a polycarbonate diol, a polycarbonate triol, a polycarbonate polyol having four or more hydroxyl groups, or any combination thereof. The polycarbonate polyol may be a linear chain. Preferred linear polycarbonate polyols have hydroxyl groups on each end. The polycarbonate polyol may be a branched or hyper branched polymer having three or more terminal ends. Preferably two or more, three or more, or even all of the terminal ends of the branched or hyper branched polycarbonate polyol include a hydroxyl group.

Examples of polycarbonate polyols and methods for producing polycarbonate polyols include those described in U.S. Pat. No. 3,689,462 A (published Sep. 5, 1972 by Maximovich, see for example column 1, line 25 to column 8, line 35), U.S. Pat. No. 4,533,729 (published Aug. 6, 1985 by Newland et al., see for example column 1, line 54 to column 4, line 53), U.S. Pat. No. 5,288,839 A (published Feb. 22, 1994 by Greco, see for example column 2, line 12 to column 5 line 2), U.S. Pat. No. 5,527,879 A (by Nakae et al., issued Jun. 18, 1996, see for example, abstract and column 2 line 9 to column 3, line 48), U.S. Pat. No. 6,872,797 B2 (issued Mar. 29, 2005 by Ueno et al., see for example col. 5, line 44 to col. 16, line 65, and col. 19, line 20 to col. 24, line 55), and U.S. Pat. No. 8,779,040 B2 (issued Jul. 15, 2014 by van der Weele et al., see for example column 5, line 12 to column 15, line 32) and in US Patent Application Publication Nos. US Patent Application Publications US 2003/0176622 A1 (published on Sep. 18, 2003 by Konishi et al., see for example paragraphs 8-74), US20040092699 A1 (published May 13, 2004 by Ueno et al., see for example abstract, paragraphs 2-8, 13-37, and 39-151), US2008/0146766 A1 (published Jun. 19, 2008 by Masubuchi et al., see for example the abstract and paragraphs 13-54), and US20080167430 A1 (published Jul. 10, 2008 by Bruchmann et al., see for example paragraphs 3-149), the contents of which are each incorporated herein by reference.

The polycarbonate polyol may be a homopolymer or a copolymer. The polycarbonate polyol may include, consist essentially of, or consist entirely of repeating structural carbonate units (which may be the same or different) of the formula:

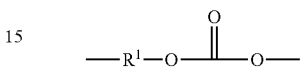

wherein the $R^1$ group preferably are aliphatic, alicyclic, aromatic, or any combination thereof. Preferably at least about 60 percent of the total number of $R^1$ groups are aromatic organic radicals and the balance thereof are aliphatic, alicyclic, or aromatic radicals. In one aspect, each $R^1$ is an aromatic organic radical, for example a radical of the formula: -$A^1$-$Y^1$-$A^2$- wherein each of $A^1$ and $A^2$ is a monocyclic divalent aryl radical and Y' is a bridging radical having one or two atoms that separate $A^1$ from $A^2$. For example, one atom separates $A^1$ from $A^2$. Illustrative non-limiting examples of radicals of this type are —O—, —S—, —S(O)—, —S(O2)—, —C(O)—, methylene, cyclohexylmethylene, 2-[2.2.1]-bicycloheptylidene, ethylidene, isopropylidene, neopentylidene, cyclohexylidene, cyclopentadecylidene, cyclododecylidene, and adamantylidene. The bridging radical Y' may be a hydrocarbon group or a saturated hydrocarbon group such as methylene, cyclohexylidene, or isopropylidene.

Polycarbonates may be produced by the interfacial reaction of dihydroxy compounds having the formula HO—$R^1$—OH, wherein $R^1$ is as defined above. Dihydroxy compounds suitable in an interfacial reaction include the dihydroxy compounds of formula (A) as well as dihydroxy compounds of the formula HO-$A^1$-$Y^1$-$A^2$-OH wherein Y1, $A^1$ and $A^2$ are as described above. Also included are bisphenol compounds of the general formula:

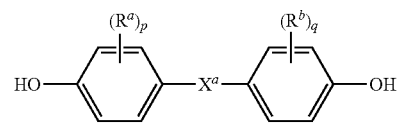

wherein $R^a$ and $R^b$ each represent a halogen atom or a monovalent hydrocarbon group and may be the same or different; p and q are each independently integers of 0 to 4; and $X^a$ represents one of the groups of the formula:

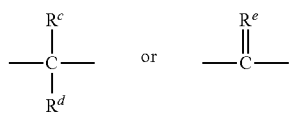

wherein $R^c$ and $R^d$ each independently represent a hydrogen atom or a monovalent linear or cyclic hydrocarbon group and $R^e$ is a divalent hydrocarbon group.

Some illustrative, non-limiting examples of suitable dihydroxy compounds include the following: resorcinol, hydroquinone, 4,4'-dihydroxybiphenyl, 1,6-dihydroxynaphthalene, 2,6-dihydroxynaphthalene, bis(4-hydroxyphenyl) methane, bis(4-hydroxyphenyl)diphenylmethane, bis(4-hydroxyphenyl)-1-naphthylmethane, 1,2-bis(4-hydroxyphenyl)ethane, 1,1-bis(4-hydroxyphenyl)-1-phenylethane, 2-(4-hydroxyphenyl)-2-(3-hydroxyphenyl)propane, bis(4-hydroxyphenyl)phenylmethane, 1,1-bis(hydroxyphenyl) cyclopentane, 1,1-bis(4-hydroxyphenyl)cyclohexane, 1,1-bis(4-hydroxyphenyl)isobutene, 1,1-bis(4-hydroxyphenyl) cyclododecane, trans-2,3-bis(4-hydroxyphenyl)-2-butene, 2,2-bis(4-hydroxyphenyl)adamantine, (alpha,alpha'-bis(4-hydroxyphenyl)toluene, bis(4-hydroxyphenyl)acetonitrile, 2,2-bis(3-methyl-4-hydroxyphenyl)propane, 2,2-bis(3-ethyl-4-hydroxyphenyl)propane, 2,2-bis(3-n-propyl-4-hydroxyphenyl)propane, 2,2-bis(3-isopropyl-4-hydroxyphenyl)propane, 2,2-bis(3-sec-butyl-4-hydroxyphenyl)propane, 2,2-bis(3-t-butyl-4-hydroxyphenyl)propane, 2,2-bis(3-cyclohexyl-4-hydroxyphenyl)propane, 2,2-bis(3-allyl-4-hydroxyphenyl)propane, 2,2-bis(3-methoxy-4-hydroxyphenyl)propane, 4,4'-dihydroxybenzophenone, 3,3-bis(4-hydroxyphenyl)-2-butanone, 1,6-bis(4-hydroxyphenyl)-1,6-hexanedione, ethylene glycol bis(4-hydroxyphenyl)ether, bis(4-hydroxyphenyl)ether, bis(4-hydroxyphenyl)sulfide, bis(4-hydroxyphenyl)sulfoxide, bis(4-hydroxyphenyl)sulfone, 9,9-bis(4-hydroxyphenyl)fluorine, 2,7-dihydroxypyrene, 6,6'-dihydroxy-3,3,3',3'-tetramethylspiro(bis)indane ("spirobiindane bisphenol"), 3,3-bis(4-hydroxyphenyl) phthalide, 2-phenyl-3,3-bis(4-hydroxyphenyl)phthalimidine (PPPBP), 2,6-dihydroxydibenzo-p-dioxin, 2,6-dihydroxythianthrene, 2,7-dihydroxyphenoxathin, 2,7-dihydroxy-9,10-dimethylphenazine, 3,6-dihydroxydibenzofuran, 3,6-dihydroxydibenzothiophene, and 2,7-dihydroxycarbazole, and the like, as well as combinations comprising at least one of the foregoing dihydroxy compounds.

Specific examples of the types of bisphenol compounds that may be represented by formula (3) include 1,1-bis(4-hydroxyphenyl)methane, 1,1-bis(4-hydroxyphenyl)ethane, 2,2-bis(4-hydroxyphenyl)propane (hereinafter "bisphenol-A" or "BPA"), 2,2-bis(4-hydroxyphenyl) butane, 2,2-bis(4-hydroxyphenyl)octane, 1,1-bis(4-hydroxyphenyl)propane, 1,1-bis(4-hydroxyphenyl) n-butane, 2,2-bis(4-hydroxy-1-methylphenyl) propane, and 1,1-bis(4-hydroxy-t-butylphenyl)propane. Combinations comprising at least one of the foregoing dihydroxy compounds may also be used.

The polycarbonate may be a linear polycarbonate or a branched polycarbonate. The branched polycarbonates may be prepared by adding a branching agent during polymerization. These branching agents include polyfunctional organic compounds containing at least three functional groups, preferably selected from hydroxyl, carboxyl, carboxylic anhydride, haloformyl, and mixtures of the foregoing functional groups. The branching agents may be added at a level of about 0.05 weight percent or more, preferably about 0.10 weight percent or more, based on the total weight of the polycarbonate. The amount of the branching agent(s), may be about 10 weight percent or less, preferably about 2 weight percent or less. All types of polycarbonate end groups are contemplated as being useful in the polycarbonate composition, provided that such end groups do not significantly affect desired properties of the thermoplastic.

Suitable polycarbonates can be manufactured by processes such as interfacial polymerization and melt polymerization. Although the reaction conditions for interfacial polymerization may vary, an exemplary process generally involves dissolving or dispersing a dihydric phenol reactant in aqueous caustic soda or potash, adding the resulting mixture to a suitable water-immiscible solvent medium, and contacting the reactants with a carbonate precursor in the presence of a suitable catalyst such as triethylamine or a phase transfer catalyst, under controlled pH conditions, e.g., about 8 to about 10. The most commonly used water immiscible solvents include methylene chloride, 1,2-dichloroethane, chlorobenzene, toluene, and the like. Suitable carbonate precursors include, for example, a carbonyl halide such as carbonyl bromide or carbonyl chloride, or a haloformate such as a bishaloformate of a dihydric phenol (e.g., the bischloroformates of bisphenol A, hydroquinone, or the like) or a glycol (e.g., the bishaloformate of ethylene glycol, neopentyl glycol, polyethylene glycol, or the like). Combinations comprising at least one of the foregoing types of carbonate precursors may also be used.

Polycarbonate diols and polycarbonate polyols as used herein further includes copolymers comprising carbonate chain units. A polycarbonate copolymer may include, consist essentially of or consist entirely of carbonate chain units. A polycarbonate copolymer may additionally include one or more repeat units that are not carbonates. For example, the polycarbonate copolymer may include a polyester, such as in a copolyester-polycarbonate. Such copolymers may include repeating units of the formula:

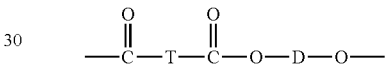

wherein D is a divalent radical derived from a dihydroxy compound, and may be, for example, a $C_{2-10}$ alkylene radical, a $C_{6-20}$ alicyclic radical, a $C_{6-20}$ aromatic radical or a polyoxyalkylene radical in which the alkylene groups contain 2 to about 6 carbon atoms, specifically 2, 3, or 4 carbon atoms; and T is a divalent radical derived from a dicarboxylic acid, and may be, for example, a $C_{2-10}$ alkylene radical, a $C_{6-20}$ alicyclic radical, a $C_{6-20}$ alkyl aromatic radical, or a $C_{6-20}$ aromatic radical.

Diene Polyol

The polyol may include, consist essentially of, or consist entirely of one or more diene polyols. The diene polyol preferably includes one or more dienes in an amount of about 40 weight percent or more, more preferably about 70 weight percent or more and most preferably about 90 weight percent or more. The diene preferably is a diene having from about 4 to about 20 carbon atoms, more preferably about 4 to about 8 carbon atoms, and most preferably 4 carbon atoms.

A particularly preferred diene polyol is a polybutadiene polyol. The polybutadiene polyol preferably includes about 40 weight percent or more butadiene repeat units. The butadiene may be present as 1-2 additions, cis 1-4 additions, 1-4 trans additions, or any combination thereof. Preferably the amount of 1-2 additions is about 50 percent or less, more preferably about 40 percent or less and most preferably about 30 percent or less based on the total number of butadiene repeat units in the polyol.

Carbinol Terminated Polyalkyl Siloxane

The central polymer portion may include a carbinol terminated polyalkyl siloxane. Preferred polyalkyl siloxanes have one or preferably two alkyl groups on each silicon atom. Preferred alkyl groups are $C_{1-10}$ hydrocarbons. More preferably the alkyl group includes or consists entirely of ethylene. A particularly preferred polyalkyl siloxane is poly-dimethylsiloxane. The polyalkyl siloxane may be linear or branched. Preferably each chain end includes a hydroxyl group.

Polyalkylene Glycol

The central polymer portion may include a polyalkylene glycol. The polyalkylene glycol preferably includes, consists essentially of or consists entirely of one or more alkylene glycols having from 2 to 10 carbon atoms. Preferably the amount of the $C_2$-$C_{10}$ alkylene glycols is about 50 weight percent or more, more preferably about 80 weight percent or more, even more preferably about 90 weight percent or more, and most preferably about 95 weight percent or more. The polyalkylene glycol may include linear polymer, branched polymer, or both. Preferably, the polyalkylene glycol includes a hydroxyl group at each end of the polymer. Branched polymers may have 3, 4, 5, 6, 7, or more chain ends. Hyperbranched polymers may have about 8 chain ends or more, about 15 chain ends or more, or about 20 chain ends or more.

Preferred polyalkylene glycols include ethylene glycol, butylene glycol, propylene glycol, or any combination thereof. The total amount of ethylene glycol, propylene glycol, or butylene glycol preferably is about 50 weight percent or more, more preferably about 85 weight percent or more, even more preferably about 92 weight percent or more, and most preferably about 97 weight percent or more, based on the total weight of the polyalkylene glycol.

The central portion may include an ethoxylate having two or more hydroxyl groups. For example, the ethoxylate may be an ethoxylate of an aliphatic compound, or an aromatic compound. The ethoxylate may include any number of ethylene oxide groups. Preferably the ethoxylate includes one or more ethylene oxide groups for each hydroxyl group. The ethoxylate may be a linear compound or may be branched. An example of a branched ethoxylate is a glycerol ethoxylate.

The central polymer portion may include a cyclic polyol. The cyclic polyol preferably includes, consists essentially of or consists entirely of N—C=O cyclic structure as a backbone and one or more hydroxyl groups preferably 3 ethyl hydroxyl groups. An example of a cyclic polyol is 1,3,5-Tris(2-Hydroxyethyl)isocyanurate.

Functional Compound

The composition disclosed include 1,1 disubstituted-1-alkene compounds which preferably are 1,1 dicarbonyl substituted alkene compounds. Preferred 1,1 dicarbonyl substituted alkene compounds are 1,1-dicarbonyl substituted ethylene compounds. 1,1-dicarbonyl substituted ethylene compounds refer to compounds having a carbon with a double bond attached thereto and which is further bonded to two carbonyl carbon atoms. Exemplary compounds are shown in Formula 1:

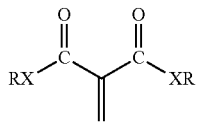

wherein R is a hydrocarbyl group which may contain one or more heteroatoms and X is oxygen or a direct bond (such as a methylene β-ketoester). Exemplary classes of 1,1-dicarbonyl substituted ethylenes are the methylene malonates, methylene beta-keto ester or diketones. Methylene malonates are exemplified by formula 2:

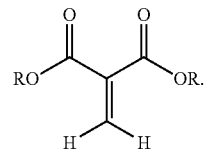

R may be separately in each occurrence alkyl, alkenyl, $C_3$-$C_9$ cycloalkyl, heterocyclyl, alkyl heterocyclyl, aryl, aralkyl, alkaryl, heteroaryl, or alkheteroaryl, or polyoxyalkylene, or both of the Rs form a 5-7 membered cyclic or heterocyclic ring. R may be separately in each occurrence $C_1$-$C_{15}$ alkyl, $C_2$-$C_{15}$ alkenyl, $C_3$-$C_9$ cycloalkyl, $C_{2-20}$ heterocyclyl, $C_{3-20}$ alkheterocyclyl, $C_6$-$C_{18}$ aryl, $C_7$-$C_{25}$ alkaryl, $C_{7-25}$ aralkyl, $C_{5-18}$ heteroaryl or $C_{6-25}$ alkyl heteroaryl, or polyoxyalkylene, or both of the R groups form a 5-7 membered cyclic or heterocyclic ring. The recited groups may be substituted with one or more substituents, which do not interfere with the reactions disclosed herein. Preferred substituents include halo alkylthio, alkoxy, hydroxyl, nitro, azido, cyano, acyloxy, carboxy, or ester. R may be separately in each occurrence $C_1$-$C_{15}$ alkyl, $C_3$-$C_6$ cycloalkyl, $C_4$-$C_{18}$ heterocyclyl, $C_4$-$C_{18}$ alkheterocyclyl, $C_6$-$C_{18}$ aryl, $C_7$-$C_{25}$ alkaryl, $C_{7-25}$ aralkyl, $C_{5-18}$ heteroaryl or $C_{6-25}$ alkyl heteroaryl, or polyoxyalkylene. R may be separately in each occurrence a $C_1$-$C_4$ alkyl. R may be separately in each occurrence methyl or ethyl. R may be the same for each ester group on the 1,1-dicarbonyl substituted ethylenes. Exemplary compounds are dimethyl, diethyl, ethylmethyl, dipropyl, dibutyl, diphenyl, and ethyl-ethylgluconate malonates; or dimethyl and diethyl methylene malonate (R is either methyl or ethyl).

The 1,1-dicarbonyl substituted ethylene compounds disclosed herein exhibit a sufficiently high purity so that it can be polymerized. The purity of the 1,1-dicarbonyl substituted ethylenes may be sufficiently high so that 70 mole percent or more, preferably 80 mole percent or more, more preferably 90 mole percent or more, even more preferably 95 mole percent or more, and most preferably 99 mole percent or more of the 1,1-dicarbonyl substituted ethylenes is converted to polymer during a polymerization process. The purity of the 1,1-dicarbonyl substituted ethylenes is about 96 mole percent or greater, about 97 mole percent or greater, about 98 mole percent or greater, about 99 mole percent or greater, or about 99.5 mole percent or greater, based on the total weight of the 1,1-dicarbonyl substituted ethylenes. The 1,1-dicarbonyl substituted ethylenes contain 4 mole percent or less of 1,1-dicarbonyl substituted-1,1 bis (hydroxymethyl)-methanes, 3 mole percent of less of 1,1-dicarbonyl substituted-1,1 bis (hydroxymethyl)-methanes, 2 mole percent of less of 1,1-dicarbonyl substituted-1,1 bis (hydroxymethyl)-methanes, 1 mole percent of less of 1,1-dicarbonyl substituted-1,1 bis (hydroxymethyl)-methanes, or 0.5 mole percent of less of 1,1-dicarbonyl substituted-1,1 hydroxymethyl-methanes. The concentration of any impurities containing a dioxane group preferably is about 2 mole percent or less, more preferably about 1 mole percent or less, even more preferably about 0.2 mole percent or less, and most preferably about 0.05 mole percent or less, based on the total weight of the 1,1-dicarbonyl substituted ethylenes. The total concentration of any impurity having the alkene group replaced by an analogous hydroxyalkyl group (e.g., by a Michael addition of the alkene with water) preferably is about 3 mole percent or less, more preferably about 1 mole percent or less, even more preferably about 0.1 mole percent or less, and most preferably about 0.01 mole percent or less, based on the total moles in the 1,1-dicarbonyl substituted ethylenes. Preferred 1,1-dicarbonyl substituted ethylenes are prepared by a process including one or more (e.g., two or more) steps of distilling a reaction product or an intermediate reaction product (e.g., a reaction product or intermediate reaction product of a source of formaldehyde and a malonic acid ester).

The functional compound may include one or more methylene malonates which may be the same or different.

Catalyst

The transesterification reactions according to the teachings herein are typically performed in the presence of one or more catalysts. The transesterification catalyst may be an acid, an ester of such acid or an enzyme. The transesterification catalyst may be an enzyme. The transesterification catalyst may be a lipase enzyme. A transesterification process utilizing an enzyme is disclosed in US 2014/0329980, incorporated herein by reference for all purposes in its entirety.

The transesterification catalyst may be one or more acids having a pKa in a polar aprotic solvent of about −5 to about 14 or esters of the acids. The acid or the ester of the acid may be present in an amount of about 3.0 molar equivalents or less of the acid or the ester of acid per molar equivalent of the ester containing compounds transesterified. When the catalyst is an acid or an ester of an acid the method may be performed at a temperature of about 20° C. to about 160° C. The transesterification catalyst may be a lipase enzyme catalyst. When the catalyst is a lipase enzyme catalyst the transesterification step is performed at an elevated temperature between about 20° C. and 70° C. During the transesterification reaction, volatile by-products may be formed and removed from the reaction mixture. The volatile by-products may be removed from the reaction mixture by applying a vacuum. The volatile by-products may be alcohols.

The catalyst may be an acid or an ester thereof. The transesterification process using an acid or ester is disclosed in U.S. patent application Ser. No. 14/814,961 filed Jul. 31, 2015, incorporated herein by reference for all purposes in its entirety. Any acid or ester thereof that catalyzes transesterification while minimizing side reactions may be used. In some embodiments, the acid or acid utilized to form an ester is an acid having a pKa in a polar aprotic solvent, such as acetonitrile or dioxane, as disclosed hereinafter. In particular, the pKa is chosen to efficiently catalyze the transesterification reaction while minimizing side reaction and the concentration of catalyst in a reaction mixture. The acid used may have a pKa of about −5 or greater, about −3 or greater, or about 1.0 or greater. The acid used may have a pKa of about 14 or less, about 11 or less, or about 9 or less. The acid can be a Bronsted acid having a pKa as disclosed. The catalyst may be a superacid or an ester thereof. Superacid means an acid having an acidic strength greater than the strength of 100 percent sulfuric acid. Ester thereof, in the context of the acid catalysts, refer to compounds wherein the hydrogen on the acid is replaced with a hydrocarbyl group, preferably an alkyl group. Superacids are acids having a strength greater than the strength of 100 percent sulfuric acid, a pKa less than 100 percent sulfuric acid, that is less than 8, more preferably less than about 5, and most preferably less than about 2. The measurement of acid strength is based on Kutt et al. "Equilibrium Acidities of Super Acids," Journal of Organic Chemistry Vol 76 pages 391 to 395, 2011, published on the Web Dec. 17, 2010, which is incorporated herein by reference. Exemplary super acids include trifluoromethanesulfonic acid (triflic acid), sulfated tin oxide, triflated tin oxide, sulfated zirconia, triflated zirconia, and triflated HZSM-5. The most preferred super acids are triflic acid and fluorosulfonic acid.

Exemplary acid catalysts include triflic acid, fluorosulfonic acid, and sulfuric acid. For reactions requiring monosubstitution (only one hydroxyl group on the alcohol is being replaced by transesterification), weaker acids with pKa values equal to or higher than sulfuric acid may be desired. Examples of such acids include sulfuric acid or methanesulfonic acid. For reactions requiring disubstitution (two hydroxyl groups on the alcohol are being replaced by transesterification), stronger acids with pKa values equal to or lower than sulfuric acid may be desired. Examples of such acids include sulfuric acid, fluorosulfonic acid, and triflic acid. For reactions requiring polysubstitution (more than 2 hydroxyl groups on the alcohol), choice of acid catalysts can be similar to that for disubstitution reactions but reaction time may need to be increased. Esters of acids useful as catalysts include alkyl triflates.

The catalyst can be mixed with the reactants or can be supported on a substrate such as a membrane or an inert carrier such as a porous support structure (the catalysts can be heterogeneous). Catalysts which are not supported are commonly referred to as homogeneous. The catalyst can be used in any concentration that catalyzes the transesterification reaction. The amount of catalyst utilized for the reaction depends on the type of catalyst being chosen. The concentration of catalyst is about 3 molar equivalents or less per equivalent of the ester compounds undergoing transesterification; about 1 molar equivalents or less; about 0.5 molar equivalents or less; about 0.1 molar equivalents or less. The concentration of catalyst is about 0.01 molar equivalents or greater per equivalent of the ester compounds undergoing transesterification; and most preferably about 0.1 molar equivalents or greater. Higher concentrations of catalysts than recited may be utilized. As disclosed in Malofsky et al., U.S. Pat. No. 8,609,885 and U.S. Pat. No. 8,884,051; and Malofsky et al. WO 2013/059473 the presence of acid in the 1,1-disubstituted alkene compounds recovered can present problems with respect to use of the compounds and low concentrations of acid in the products in use is desired. If high levels of acid are contained in the final product, additional purification or removal steps may be required. The amounts recited achieve the balance between efficient catalysis and the need for low acid concentrations in the product for use. In embodiments when the catalyst is selected from sulfuric acid or those acids having pKa values less than that of sulfuric acid, the concentration of such catalysts in the reaction mixture is preferably at the upper end of the ranges recited herein.

The catalyst may include or consist entirely of an enzymatic catalyst. Any enzymatic catalyst suitable for catalyzing the transesterification reaction may be used. Various enzymatic catalysts are described in U.S. Pat. No. 7,972,822 B2 (by Gross et al., issued on Jul. 5, 2011, see for example column 8, lines 2-4 and 7-35), U.S. Pat. No. 5,416,927 A (by Zaks et al., issued May 31, 1994, see for example column 2, line 64 to column 3, line 12), U.S. Pat. No. 5,288,619 A (by Brown et al., issued Feb. 22, 1994, see for example column 4, line 18 to column 5, line 17), US Patent Application Publication 2016/177,349 A1 (by Addy et al., published Jun. 23, 2016, see for example paragraphs 0046-0048), U.S. Patent Application Publication 2014/0017741 A1 (by Nielsen et al., published Jan. 16, 2014, see for example paragraphs 0026-0029); the contents of which are each incorporated herein by reference.

Many different enzymes may be employed in enzymatic catalytic transesterification reactions for wax esters, including those that are derived/obtained from biological organisms, those made synthetically, and those that are entirely artificial, whether made biologically and/or synthetically. For those enzymes that are lipases, these may include, one, some, any, or any combination of lipases derived from the following organisms: *Aspergillus niger, Aspergillus oryzae, Bacillus subtilis, Bacillus thermocatenulatus, Burkholderia cepacia, Burkholderia glumae, Candida rugosa, Candida antarctica* A, *Candida antarctica* B, *Candida cylindracea, Candida parapsilosis, Chromobacterium viscosum, Geotrichum candidum, Geotrichum* sp., *Mucor miehel, Humicola lanuginose, Penicillium camembertii, Penicillium chrysogenum, Penicillium roguefortii, Pseudomonas cepacia, Pseudomonas aeruginosa, Pseudomonas fluorenscens, Pseudomonas fragi, Pseudomonas alcaligenes, Pseudomonas mendocina, Rhizopus arrhizus, Rhizomucor miehe, Staphylococcus hyicus, Staphylococcus aereus, Staphylococcus epidermidis, Staphylococcus warneria, Staphylococcus xyloses, Thermomyces lanuginosus, Aspergillus* sp., *Bacillus* sp., *Burkholderia* sp., *Candida* sp., *Chromobacterium* sp., *Geotrichum* sp, *Mucor* sp, *Humicola* sp, *Penicillium* sp, *Pseudomonas* sp, *Rhizopus* sp., *Staphylococcus* sp, and *Thermomyces* sp. The lipase may include or consist essentially of one or any combination of the following: a lipase from *Thermomyces lanuginosus* marketed under the tradenames LIPOZYME TL IM or LIPEX by Novozymes A/S of Bagsvaerd, Denmark and immobilized on a substrate also manufactured by Novozymes; the lipase may be that marketed under the tradename NOVOZYM by Novozymes, A/S derived from *Candida antarctica*; those marketed under the tradenames CALB L, NOVOZYME 435, NOVOCOR AD L, AND LIPOLASE 100L by Novozymes; those marketed under the tradenames CALB, CALA, and CRL by c-LEcta, GMBH of Leipzig, Germany; those marketed under the tradenames LIPASE A "AMANO" 12, LIPASE AY "AMANO" 30SD, LIPASE G "AMANO" 50, LIPASE R "AMANO", LIPASE DF "AMANO" 15, LIPASE MER "AMANO", and NEWLASE F by Amano Enzyme Inc. of Nagoya, Japan; those marketed under the tradenames LIPASE MY, LIPASE OF, LIPASE PL, LIPASE PLC/PLG, LIPASE QLM, LIPASE QLC/QLG, LIPASE SL, and LIPASE TL by Meito Sangyo Co., Ltd., of Nagoya, Japan, a lipase from *Candida antarctica* A, a lipase from *Candida antarctica* B, and a lipase from *Candida rugosa*. In various implementations, the lipases preferably have at least 60%, at least 70%, at least 80%, at least 90%, at least 95%, at least 96%, at least 97%, at least 98%, or even at least 99% identity to any of the lipases disclosed herein, and in the patent applications disclosed herein, all of which have been previously incorporated by reference.

Polymerizable System

One aspect according to the teachings herein, is directed at a polymerizable system including the functionalized polymer and one or more methylene malonate monomers. The methylene malonate monomer may be selected so that it will copolymerize with the alkenyl groups of the functionalized polymer. It will be appreciated that the copolymerization of the functionalized polymer and one or more methylene malonate monomers may result in a block copolymer including a first polymer block including, consisting substantially of, or consisting entirely of the methylene malonate monomer(s) and a second polymer block including, consisting substantially of, or consisting entirely of the central polymer portion (e.g., a polyol containing polymer). If the functionalized polymer includes two or more spaced apart alkenyl groups (e.g., spaced apart methylene malonate compounds, preferably on different ends of the central polymer portion), the functionalized polymer may provide cross-linking of the methylene malonate monomers.

Any of the methylene malonate compounds described herein with respect to the functional compound having an alkenyl group for the functionalized polymer may be employed for the monomer in the polymerizable composition. It will be appreciated that methylene malonate monomer may be replaced in part or in whole with dimers, trimers, or longer oligomers (e.g., having a degree of polymerization of about 4 to 50, about 4 to 15, or about 4 to 8).

The second polymer block (e.g., a block including the polyol containing polymer) may be more flexible than the first polymer block and provide flexibility and/or impact resistance to the block copolymer.

The polymerizable system may include a sufficient amount of a stabilizer to prevent or minimize polymerization of the polymerizable system. The process may include a step of activating the polymerizable system for polymerizing the methylene malonate monomers and alkenyl group(s) attached to the central polymer portion.

The amount of the one or more methylene malonate monomers in the first polymer block preferably is about 20 weight percent or more, more preferably about 50 weight percent or more, even more preferably about 75 weight percent or more, and most preferably about 85 weight percent or more, based on the total weight of the first polymer block. The amount of the one or more methylene malonate monomers in the first polymer block may be about 100 weight percent or less, about 99 weight percent or less, about 97 weight percent or less, about 93 weight percent or less, or about 88 weight percent or less, based on the total weight of the first polymer block.

The amount of the polyol in the second polymer block preferably is about 25 weight percent or more, more preferably about 60 weight percent or more, even more preferably about 80 weight percent or more, and most preferably about 90 weight percent or more, based on the total weight of the second polymer block. The amount of the polyol in the second polymer block may be about 100 weight percent or less, about 98 weight percent or less, about 96 weight percent or less, or about 94 weight percent or less, based on the total weight of the second polymer block.

The ratio of the weight of the one or more methylene malonate monomers to the weight of the functionalized polymer may be about 0.05 or more, about 0.10 or more about 0.20 or more or about 0.45 or more, or about 0.60 or more. The ratio of the weight of the one or more methylene malonate monomers to the weight of the functionalized polymer may be about 0.99 or less, about 0.96 or less, about 0.92 or less, about 0.88 or less, about 0.84 or less, or about 0.80 or less.

The functionalized polymer and/or polymerizable system may be used for a film or coating. The film or coatings may have a thickness of about 0.001 µm or more, about 0.1 µm or more, about 1 µm or more, or about 2 µm or more. The coating or film preferably has a thickness of about 200 µm or less, more preferably about 50 µm or less, and most preferably about 20 µm or less.

The functionalized polymer and/or polymerizable systems according to the teachings herein may be employed in a cross-linked polymer. The cross-linked polymer may include, consist essentially of, or consist entirely of the functionalized polymer and polymerized 1,1-di-substituted alkene monomer (e.g., a methylene malonate monomer). The total amount of the functionalized polymer and the polymerized 1,1-di-substituted alkene monomer in the cross-linked polymer may be about 5 weight percent or more, about 20 weight percent or more, about 45 weight percent or more, about 70 weight percent or more, or about 90 weight percent or more, based on the total weight of the cross-linked polymer. The total amount of the functionalized polymer and the polymerized 1,1-disubstituted alkene monomer in the cross-linked polymer may be about 100 weight percent or less, or about 98 weight percent or less, based on the total weight of the cross-linked polymer.

Process

The functionalized polymers may be prepared by reacting a polymer including a polyol and having 1, 2, 3 or more hydroxyl groups with one or more functional compounds including an alkenyl group. The functional compound may include an ester group which reacts by a transesterification reaction:

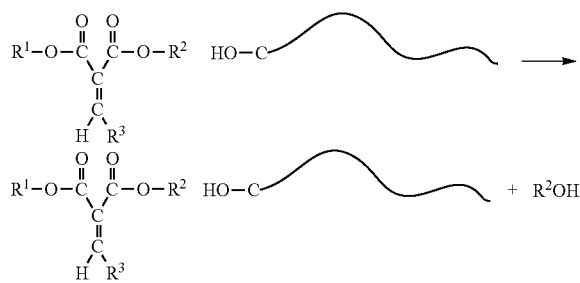

The process may employ a catalyst for accelerating the transesterification reaction. Preferred catalysts for reacting a polyol based polymer with a functional compound including an ester include an enzymatic catalyst or an acid catalyst.

The process may be a batch process, a continuous process, or a combination thereof. For example, a continuous process may include a step of feeding one or more reactants (e.g., the 1,1-disubstituted compound, and a compound that forms the central portion) into a continuous reactor. A catalyst may be fed into the reactor or the reactor may be provided with a catalyst. For example, at least a portion of the reactor may include a packing having a catalyst, or a catalyst may be present on a surface in the reactor (e.g., a surface of the reactor or a surface of a component in the reactor). The continuous reactor may be a tube reactor or other reactor suitable for inserting at least one reactant in one end and removing at least one reaction product at the opposite end. Preferably, the continuous reactor is a tube reactor including a catalyst packed in the reactor. The continuous process preferably is at a temperature of about 10° C. or more, more preferably about 15° C. or more, and most preferably about 20° C. or more. The reaction temperature preferably is about 150° C. or less. When an acid catalyst is employed, the reaction temperature preferably is about 40° C. to about 150° C., more preferably about 60° C. to about 150° C. When an enzyme catalyst is employed, the reaction temperature preferably is about 80° C. or less, more preferably about 70° C. or less, and most preferably about 60° C. or less.

The process for polymerizing a composition including one or more methylene malonate monomers and one or more functionalized polymers (e.g., including a polyol) for forming a block copolymer may employ any polymerization method suitable for polymerizing methylene malonate monomers. The functional groups on the functionalized polyol preferably including alkenyl groups suitable for anionic polymerizable. Preferably, the functional groups include methylene malonates that are the same or different from the methylene malonate monomer. More preferably, the functional groups include a methylene malonate that is also employed as a monomer in the polymerization process for forming a block copolymer.

The transesterification process may be employed to react each of the hydroxyl groups (e.g., each of the terminal hydroxyl groups) of the polyol polymer with an 1,1-disubstituted alkene compound to form a functionalized polymer. If a 1,1-disubstituted alkene reacts with two different polyol polymers, it may extend the length of the polyol polymer and add an alkenyl group in the central polymer portion of the functionalized polymer. It may be advantageous to avoid such chain extending reactions. Chain extension reactions during the formation of the functionalized polymer may be reduced, substantially eliminated, or entirely eliminated by the selection of the 1,1-disubstituted alkene compound, by the use of an excess of the 1,1-disubstituted alkene compound, or both. For example, the 1,1-disubstituted alkene compound may include or consist essentially of compounds having a single ester group capable of transesterification. As another example, the 1,1-disubstituted alkene compound may include two or more ester groups and be present in an excess concentration so that there is unreacted 1,1-disubstituted alkene compound after the transesterification reaction. The amount of excess 1,1-disubstituted alkene compound may depend on the molecular weight of the polyol polymer, the mobility of the polyol polymer, the compatibility between the polyol polymer and the 1,1-disubstituted alkene compound, and the number of hydroxyl groups (e.g., terminal hydroxyl groups) in the polyol polymer. Preferably, there is an excess of the 1,1-disubstituted alkene compound (i.e., the number of terminal hydroxyl groups of the polyol polymer available for the transesterification reaction should be less than the number of molecules of the 1,1-disubstituted alkene compound available for the transesterification reaction). Preferably, the molar ratio of the 1,1-disubstituted alkene compound to the weight of the polyol polymer is about 1.5 or more, even more preferably about 1.9 or more, even more preferably about 2.3 or more, even more preferably about 3 or more, even more preferably about 4 or more, and most preferably about 4 or more. When the molecular weight of the polyol polymer is relatively high (e.g., the ratio of the molecular weight of the polyol polymer to the molecular weight of the 1,1-disubstituted alkene compound is about 6 or more, or about 15 or more), excess amounts of 1,1-disubstituted alkene compound may be employed to reduce the viscosity of the mixture and/or to accelerate the end capping reaction. As such, the molar ratio of the 1,1-disubstituted alkene compound to the polyol polymer may be much greater than 4 (e.g., about 10 or more, about 30 or more, or about 100 or more).

The process may include a step of separating some or all of the unreacted 1,1-disubstituted alkene compound from the end-capped polyol. It may also be desirable to minimize the amount of unreacted 1,1-disubstituted alkene compound. For these reasons, it may be desirable for the weight ratio of the 1,1-disubstuted alkene compound to be generally low (e.g., so that excess 1,1-dissubstituted alkene compound is reduced and/or can easily be removed by separation or other techniques. The ratio of the weight of the 1,1-disubstituted alkene compound to the weight of the polyol polymer preferably is about 40 or less, more preferably about 20 or less, even more preferably about 10 or less and most preferably about 5 or less. However, weight ratios higher than 40 may be employed. It will be appreciated that some unreacted 1,1-disubstituted alkene compound may be used in a polymerizable composition for copolymerizing the 1,1-disubstituted alkene compound with the alkenyl groups attached to the polyol polymer. The transesterification reaction may substantially avoid or entirely avoid reacting a 1,1-disubstituted alkene compound with multiple hydroxyl groups.

Test Methods

Any numerical values recited herein include all values from the lower value to the upper value in increments of one unit provided that there is a separation of at least 2 units between any lower value and any higher value. As an example, if it is stated that the amount of a component or a value of a process variable such as, for example, temperature, pressure, time and the like is, for example, from 1 to 90, preferably from 20 to 80, more preferably from 30 to 70, it is intended that values such as 15 to 85, 22 to 68, 43 to 51, 30 to 32 etc. are expressly enumerated in this specification. For values which are less than one, one unit is considered to be 0.0001, 0.001, 0.01 or 0.1 as appropriate. These are only examples of what is specifically intended and all possible combinations of numerical values between the lowest value and the highest value enumerated are to be considered to be expressly stated in this application in a similar manner. As can be seen, the teaching of amounts expressed as "parts by weight" herein also contemplates the same ranges expressed in terms of percent by weight. Thus, an expression in the Detailed Description of the Invention of a range in terms of at "'x' parts by weight of the resulting polymeric blend composition" also contemplates a teaching of ranges of same recited amount of "x" in percent by weight of the resulting polymeric blend composition."

Unless otherwise stated, all ranges include both endpoints and all numbers between the endpoints. The use of "about" or "approximately" in connection with a range applies to both ends of the range. Thus, "about 20 to 30" is intended to cover "about 20 to about 30", inclusive of at least the specified endpoints.

The disclosures of all articles and references, including patent applications and publications, are incorporated by reference for all purposes. The term "consisting essentially of" to describe a combination shall include the elements, ingredients, components or steps identified, and such other elements ingredients, components or steps that do not materially affect the basic and novel characteristics of the combination. The use of the terms "comprising" or "including" to describe combinations of elements, ingredients, components or steps herein also contemplates embodiments that consist essentially of the elements, ingredients, components or steps.

Plural elements, ingredients, components or steps can be provided by a single integrated element, ingredient, component or step. Alternatively, a single integrated element, ingredient, component or step might be divided into separate plural elements, ingredients, components or steps. The disclosure of "a" or "one" to describe an element, ingredient, component or step is not intended to foreclose additional elements, ingredients, components or steps.

It is understood that the above description is intended to be illustrative and not restrictive. Many embodiments as well as many applications besides the examples provided will be apparent to those of skill in the art upon reading the above description. The scope of the invention should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. The omission in the following claims of any aspect of subject matter that is disclosed herein is not a disclaimer of such subject matter, nor should it be regarded that the inventors did not consider such subject matter to be part of the disclosed inventive subject matter.

EXAMPLES

Examples 1 and 2

Example 1 is a reaction mixture including a linear aromatic polyester polyol that is capped on both terminal ends with a methylene malonate monomer and residual monomer. Example 2 is the filtrate of Example 1 after removing the residual methylene malonate monomer.

About 6 g of an aromatic polyester polyol and about 30 g of diethyl methylene malonate monomer are mixed in a round bottom flask until the polyol is dissolved or otherwise dispersed in the monomer. The aromatic polyester is TERATE® HT 5100 polyol commercially available from INVISTA and having an average of about 2.2 hydroxyl groups per molecule, a hydroxyl number of about 295 mgKOH/g, and a viscosity of about 6,000 cps at 25° C. The aromatic polyester polyol includes repeating units having aromatic groups (e.g., a residue of a bisphenol) along the backbone and ester groups.

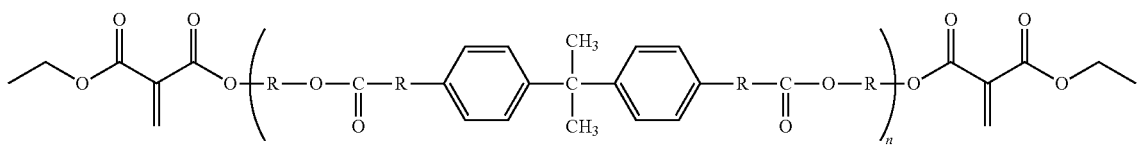

General Example of Aromatic Polyester Polyol

Figure 1B:
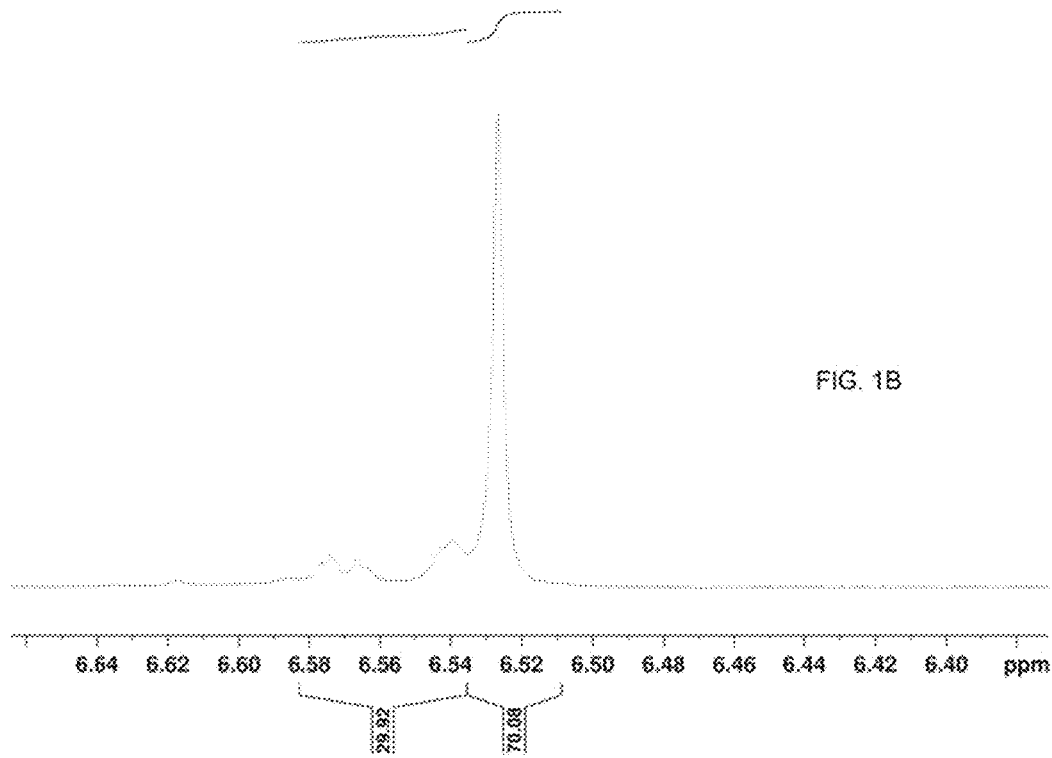
FIG. 1B is an illustrative proton NMR spectrogram of FIG. 1A enlarged in the region of the 6.5 ppm methylene region. The amount of the transesterified diethyl methylene malonate species (both monosubstituted and disubstituted) is about 29.92% and the amount of unreacted diethyl methylene malonate is about 70.08%.

About 3 g of an enzyme catalyst (about 10% by weight of diethyl methylene malonate monomer) is added to the reaction mixture. The enzyme catalyst is NOVOZYM 435 immobilized lipase enzyme commercially available from NOVOZYMES (Denmark). The round bottom flask is attached to a rotary evaporator maintained at a temperature of about 45° C. and rotated at 100 rpm for 2 hours under vacuum at 200 mm of Hg. At the end of the reaction, a small aliquot is taken for NMR analysis and the remaining mixture is filtered using a cotton plug in a 100 ml syringe to remove the enzyme. The filtrate (i.e., the reaction mixture) is a blend of about 70 weight percent diethyl methylene malonate monomer (i.e., DEMM) and about 30 weight percent end-capped aromatic polyester polymer. FIG. 1A is a proton NMR spectrogram of the reaction mixture including the DEMM. The formation of a new species with a methylene double bond is confirmed in the 6.535-6.583 ppm region of the spectrum and the residual DEMM is confirmed in the 6.51-6.535 ppm region of the spectrum, as seen in FIG. 1B.

The end capped aromatic polyester may have one or more of the features illustrated below:

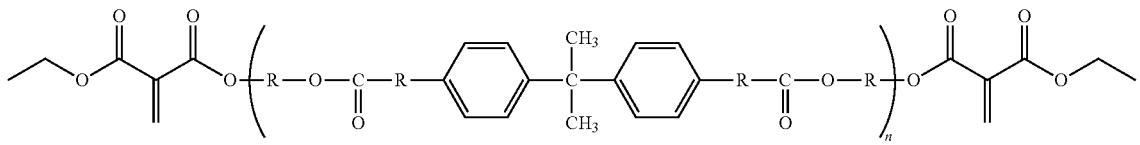

General Example of Aromatic Polyester Polyol

The reaction mixture including the residual DEMM and the end capped aromatic polyester polymer is used to make lap shears specimens on cold rolled steel panels using 0.1 wt % Na-benzoate in ethanol as an activator. Lap shear strength after room temperature cure for 24 hours is measured on at least 3 specimens. The mean lap shear strength is about 5.7 MPa. Additional lap shear specimens are cured for 24 hours at room temperature and then aged at 120° C. in an oven for 2 days. After aging, lap shear strength increased beyond 10 MPa. It is believed that the increase in lap shear strength is a result of crosslinking with heat. The aromaticity of the polyol results in an adhesive system having a bulky main chain structure with high rigidity.

A specimen of the reaction mixture including the unreacted DEMM is cured in an Aluminum pan using tetramethylguanidene (i.e., TMG) in bulk. The resultant polymer does not dissolve in dichloromethane (i.e., DCM). This indicates a high degree of crosslinking.

Example 2

Hexane is added to a specimen of the reaction mixture of Example 1 including the unreacted DEMM. Hexane is a good solvent for the residual DEMM and a bad solvent for the polyol and for the end capped polyol. The end capped polyol is separated from excess DEMM of the reaction mixture. The end capped polyol is then dried in vacuum to remove any remaining hexane. The isolated end capped aromatic polyester is then tested for adhesion properties by preparing lap shear specimens using the same cure times as for the lap shear testing of the reaction mixture. The lap shear strength of the isolated end capped polyester is about 4 MPa after curing 24 hours at room temperature cure and 6.6 MPa after curing at 120° C. for 2 days. It is believed that the bulky structure of the central polymer portion and the small concentration of the alkenyl groups makes it difficult for anionic polymerization of the isolated end capped polyol. The use of a methylene malonate monomer such as DEMM may increase the adhesion as shown in the higher adhesion of Example 1 compared to Example 2.

Example 3

Example 3 is a reaction mixture including an end capped aliphatic polyester polyol and residual methylene malonate monomer.

Example is prepared by reacting TERRIN™ 168 polyol with DEMM to end cap the polyol. TERRIN™ 168 aliphatic polyester polyol is commercially available from INVISTA and is a prepared from glycols (including diethylene glycerol, HO—C$_2$H$_4$—O—C$_2$H$_4$—OH) and carboxylic acid-functional monomers (mainly adipic acid and 6-hydroxycaproic acid).

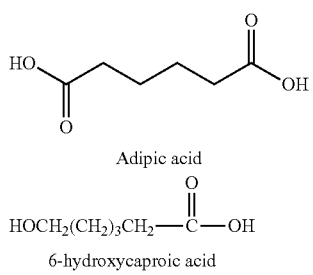

Adipic acid

HOCH$_2$(CH$_2$)$_3$CH$_2$—C(=O)—OH 6-hydroxycaproic acid

About 30 g of DEMM and about 6 g of TERRIN™ 168 (about 5:1 weight ratio) are mixed in a round bottom flask until the polyol is dissolved or dispersed in the DEMM monomer. About 3 g of NOVOZYM® 435 enzyme catalyst (about 10% by weight of the DEMM) is added to the flask. The flask is attached to a rotary evaporator maintained at 45° C. and rotated at 100 rpm for 2 hours under vacuum at 200 mm of Hg. At the end of the reaction, a small aliquot is taken for NMR analysis and the remaining mixture is filtered using a cotton plug in a 100 ml syringe to remove the enzyme. The reaction mixture (i.e., the filtrate) is a blend including the unreacted DEMM and the end capped aliphatic polyester polymer in weight ratio of about 75:25.

A specimen of the reaction mixture is cured in an Aluminum pan using tetramethyl guanidine (TMG) in bulk. The resulting polymer does not dissolve in DCM, indicating a high degree of crosslinking. After washing with DCM, the polymer is tested using thermogravimetric analysis (TGA) at a heating rate of about 10° C./min. The TGA scan is shown in FIG. 2. Decomposition resulting in weight loss begins at a temperature of about 250° C. A weight loss of 50% is at a temperature greater than about 300° C. (e.g., about 335-365° C.). In comparison, the temperature corresponding to 50 weight percent weight loss (as measured by TGA) for DEMM homopolymer typically is about 210° C., and the temperature corresponding to 50 weight percent weight loss for cross-linked DEMM (prepared by polymerizing 70 weight percent DEMM in the presence of about 30 weight percent cross-linker prepared by transesterifying DEMM with hexane diol) is above about 300° C. It is believed that these TGA results demonstrate that the end capped aliphatic polyester polyol is copolymerized with the DEMM and results in crosslinking of the DEMM.

Example 4 and Example 5

Example 4 is a reaction mixture including a polycarbonate polyol that is endcapped with a methylene malonate monomer and residual monomer. Example 5 is the endcapped polycarbonate polyol after removing the residual monomer.

Example 4 is prepared by mixing about 30 g of DEMM and about 6 g of PACAPOL™ F250 polycarbonate polyol (about 5:1 weight ratio) in a round bottom flask until the polyol is dissolved or dispersed in the DEMM monomer.

PACAOPOL™ F250 is an aliphatic polycarbonate polyol commercially available from INSTRUMENTAL POLYMER TECHNOLOGIES. PACAPOL™ F260 is slightly branched, has 100% solids, and has hydroxyl functionality, with an equivalent weight of about 225 g/eq. To facilitate the mixing of the polycarbonate polyol with the methylene malonate monomer, a solvent (e.g., toluene) may be used. About 3 g of CLEA 102B4 *candida antarctica* isoform B/powder), cross-linked enzyme aggregate (about 10% by weight of DEMM) is added to the flask as a reaction catalyst. CLEA 102B4 is commercially available from CLEA TECHNOLOGIES B.V. (Delft, The Netherlands). The flask is attached to a Rotary Evaporator and the reaction is performed at 45° C. with a rotation speed of about 100 rpm for 2 hours under a vacuum of about 200 mm of Hg. At the end of the reaction, a small aliquot is taken for NMR analysis and the remaining material is filtered using a cotton plug in a 100 ml syringe to remove the enzyme. The reaction mixture (the filtrate) includes a blend of DEMM with end capped polycarbonate polyol at a weight ratio of about 75:25.

The end capped polycarbonate polyol may have one or more of the features illustrated in the structure below:

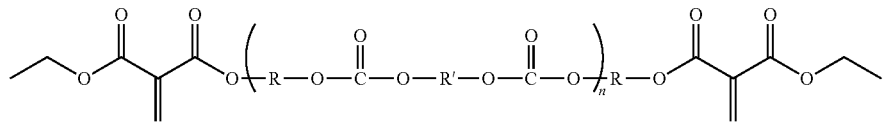

General Example of Polycarbonate Polyol

The reaction mixture is cured in an aluminum pan using TMG. The resultant polymer does not dissolve in DCM, indicating a high degree of crosslinking.

Example 5 is prepared by removing the unreacted methylene malonate monomer from Example 4. Example 5 is prepared by adding hexane to the reaction mixture of Example 4. Hexane is a bad solvent for the polycarbonate polyol and the end capped polycarbonate polyol. After removing the DEMM, the end capped polyol is dried under vacuum at room temperature to remove any remaining hexane.

The isolated capped polycarbonate polyol is cured in an Aluminum pan using TMG. The resultant polymer does not dissolve in DCM, indicating a high degree of crosslinking.

FIG. 3 is an proton NMR spectrograph of the isolated end capped polycarbonate polyol.

A coating of the reaction mixture of Example 4 (including the endcapped polycarbonate polyol and unreacted DEMM) is drawn down on a treated cold rolled steel panel. The cold rolled steel panel is treated with 0.1% Na-benzoate in BUTYL CELLOSOLVE™ solvent (commercially available DOW CHEMICAL COMPANY) for initiating the polymerization of the DEMM. The reaction mixture is drawn down using a Meyer Rod 10 and cured at room temperature for about 24 hours. The resulting coating has a thickness of about 25 μm. The coating has a high degree of flexibility as noticed by the coating maintaining adhesion when the panel is bent by about 180° on a mandrel, according to ASTM D522-93. Similar bending tests on specimens prepared with only DEMM monomer on the treated cold rolled steel panel (i.e., DEMM homopolymer) results in the coating flaking off the surface of the panel upon bending. Thus, the addition of end capped polycarbonate improves the flexibility of the product of polymerizing DEMM.

Example 6

Example 6 is a reaction mixture including a polybutadiene polyol end capped with a methylene malonate monomer and monomer.

An example of a polybutadiene polyol is shown below:

Example 6 is prepared by mixing about 40 g of DEMM and about 10 g of POLY BD® R-20LM hydroxyl terminated polybutadiene resin (i.e., HTPB) (i.e., a weight ratio of about 4:1) in a round bottom flask until the polyol is dissolved or dispersed in the DEMM monomer. POLY BD® resin is commercially available from CRAY VALLEY HYDROCARBON SPECIALTY CHEMICALS and has a number average molecular weight of about 1200, a glass transition temperature of about −70° C., and has an average of about 2.5 hydroxyl groups per chain. About 20% of the monomer units in the HTPB are 1,2 additions and about 80% are 1-4 additions. Then about 4 g of CLEA 102B4 enzyme catalyst (about 10% by weight of DEMM) is added to the flask. The flask is attached to a Rotary Evaporator maintained at about 45° C. and rotated at about 100 rpm for 2 hours under a vacuum of about 200 mm of Hg. At the end of the reaction, a small aliquot is taken for NMR analysis. The remaining material is filtered using a cotton plug in a 100 ml syringe to remove the enzyme. The reaction mixture (i.e., the filtrate) is a blend including unreacted DEMM and end capped polybutadiene at a weight ratio of about 75:25.

The end capped polybutadiene may have one or more of the features illustrated in the structure below:

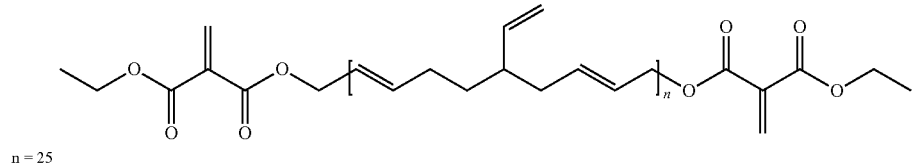

n = 25

FIG. 4 shows the H-NMR of the reaction mixture. The methylene protons next to the OH groups in HTPB typically appear at 4.1 and 4.3 ppm on the H-NMR spectrum. These are significantly reduced (e.g., disappear or appear very faint) in the reaction mixture after the transesterification reaction.

The reaction mixture is cured in an Aluminum pan using TMG. The resultant polymer does not dissolve in DCM, indicating a high degree of crosslinking.

These results confirm that end capping of polybutadiene was achieved.

Example 7

Example 7 is a reaction mixture including an end capped polybutadiene and unreacted methylene malonate monomer.

Example 7 is prepared in a continuous column reactor at a temperature of about 30° C., a pressure of about 150 mmHg, a feed flow rate of about 100 mL/hr, and a weight ratio of DEMM to HTPB of about 5:1. A stainless steel feed container is heat taped and placed on a stir plate to keep the mixture of DEMM and HTPB homogenized. Feed lines leading into the bottom of the reactor are heat taped and insulated. The reactor is jacketed and heated with an oil heater, and insulated to reduce heat loss. Temperature probes are placed at the reactor, the feed line, and the feed container to maintain 30° C. The DEMM/HTPB mixture is pumped at about 100 mL/hr using a peristaltic pump. The mixture is fed into the reactor from the bottom, comes into contact with the CLEA 102B4 enzyme, and is pumped off the top of the reactor. The reactor is filled with about 25 g of CLEA 102B4 enzyme. Vacuum is pulled from the top of the reactor, above the outlet taking off the product. The product (ie., reaction mixture) is pumped off into a collection container using a peristaltic pump and is analyzed via H-NMR every hour after the collecting of the product begins. Transesterification is confirmed by H-NMR as described above for Example 6.

The reaction mixture is cured in an Aluminum pan using TMG. The resultant polymer does not dissolve in DCM, indicating a high degree of crosslinking.

Example 8

Example 8 is a reaction mixture including a carbinol terminated polydimethyl siloxane end capped with and methylene malonate monomer and unreacted methylene malonate monomer.

Example 8 is prepared by mixing about 60 g of DEMM with about 12 g of GELEST DMS C-21 carbinol terminated poly(dimethylsiloxane) (5:1 weight ratio) in a round bottom flask until the polyol dissolved or dispersed into the DEMM monomer. GELEST DMS C-21 is commercially available from GELEST, INC. (Morrisville, Pa.), has a number average molecular weight of about 4,500 to 5,000, a specific gravity of about 0.98, and a viscosity of about 110-140 cSt. The CAS number is: 156327-07-0. About 6 g of CLEA 102B4 enzyme catalyst (10% by weight of DEMM) is added to the flask. The flask is attached to a Rotary Evaporator maintained at 45° C. and rotated at 100 rpm for 2 hours under vacuum at 200 mm of Hg. At the end of the reaction, the mixture is filtered using a cotton plug in a 100 ml syringe to remove the enzyme. The resulting reaction mixture (i.e., the filtrate) is a blend of DEMM with end capped siloxane polyol at a weight ratio of about 75-25.

The end capped siloxane polyol may have one or any combinations of the features illustrated in the structure below:

The reaction mixture is cured in an aluminum pan using TMG. The resultant polymer does not dissolve in DCM, indicating a high degree of crosslinking.

The reaction mixture of the endcapped siloxane with unreacted DEMM is drawn down on a pre-initiated (0.1% Na-benzoate in butyl cellosolve) cold rolled steel panel using a Meyer Rod 10 and is cured at room temperature for 24 hours followed by heating at 82° C. for 1 hour. The coating has a thickness of 25 µm. The coating maintains adhesion to the panel after bending by about 180° on a mandrel, according to ASTM D522-93. This indicates a high degree of flexibility of the coating.

The coating displays hydrophobic character. For example, the contact angle of water on the coating is about 70°. In comparison, a coating of only DEMM monomer drawn down on the pre-initiated cold rolled steel panel has a contact angle of water on the coating of about 55-55° (i.e., about 15-20° lower). As illustrated by example 8, an end capped polysiloxane polyol may be used to impart hydrophobicity to a coating based on a methylene malonate such as DEMM.

Example 9

Example 9 is a reaction mixture including an polyalkylene glycol end-capped with a methylene malonate monomer and unreacted methylene malonate monomer. The end-capping of the polyalkylene glycol is carried out using pegylation process.

CARBOWAX™ PEG 300 polyethylene glycol (commercially available from DOW CHEMICAL COMPANY) is purified by passing through an alumina column to residual base catalyst. The polyethylene glycol has a number average molecular weight of about 285 to 300 g/mole, a hydroxyl number of about 340 to 394 mg KOH/g, a melting range of about −15° C. to about −8° C., and a heat of fusion of about 37 cal/g. A 250 mL round bottom flask is charged with about 30 g (0.17 mol) of DEMM, about 3 g (10 wt % of the DEMM) of CLEA 102B4enzyme and about 16.6 g (0.083 mol) of the PEG 300 (alumina passed). The flask is connected to a rotary evaporator with a vacuum of about 200 mm Hg and heated to about 45° C. for 2 hrs. The vacuum removes ethanol as a reaction by-product. The enzyme is then filtered from the reaction mixture using a cotton plug in 20 ml syringe. NMR results indicate that about 35 percent of the DEMM is reacted to the PEG and about 65 percent of the DEMM remains as unreacted monomer in the reaction mixture. FIG. 5 shows the NMR for the reaction mixture.

The endcapped polymer may have a structure including a central polymer portion including a polyalkoxide and terminal methylene malonate groups having one or more (or all) of the features illustrated below:

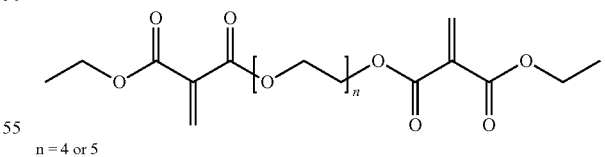

n = 4 or 5

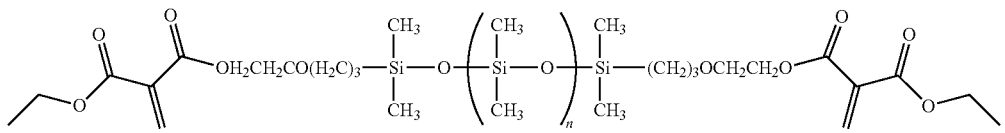

Carbinol Terminated Silicone Polyol-Gelest DMS-C21

The reaction mixture of the endcapped PEG with DEMM is drawn down on a pre-initiated (0.1% Na-benzoate in butyl cellosolve) cold rolled steel panel using a Meyer Rod 10 resulting in a 25-micron thick coating after full cure at room temperature for 24 hours followed by heating at 82° C. for 1 hour. The coating displays hydrophilic character with water wetting the surface with ease and eventually permeating through the coating layer on continued exposure. A similar coating drawn down with only DEMM monomer demonstrates no hydrophilic character. This demonstrates the hydrophilicity imparted by polyethylene glycol in DEMM based coatings.

Example 10

Example 10 is a reaction mixture including an polyalkylene glycol end-capped with a methylene malonate monomer and unreacted methylene malonate monomer. The end-capping of the polyalkylene glycol is carried out using an acid catalyzed transesterification process.

A three neck (250 mL) round bottom flask with a distillation head, thermometer, vacuum adapter, and a collection flask are assembled using high vacuum grade grease along with a heating mantle (and thermocouple) and a magnetic stir bar. To this round bottom flask set-up, a mixture of about 20 g (about 0.12 mol) of DEMM, about 4.6 g (about 0.023 mol) of CARBOWAX™ PEG 200 polyethylene glycol (commercially available from DOW CHEMICAL COMPANY), about 0.02 g (about 1000 ppm) of MeHQ and about 0.3 ml (about 0.0058 mol) of $H_2SO_4$ is charged. CARBOWAX™ PEG 200 polyethylene glycol has a weight average molecular weight of about 190 to 210 g/mole, an average hydroxyl number of about 535 to about 590 mg KOH/g, and a melting point below about −65° C. A reduced pressure of about 400 mm Hg is maintained during the reaction using a vacuum pump. The reaction mixture is then heated to about 130° C. and stirred for about 2 hours. Ethanol is collected as a reaction byproduct. The amount of endcapping of the PEG is calculated using NMR. About 45 percent of the DEMM is reacted with the PEG and about 55 percent of the DEMM remains as monomer.

The endcapped polymer may have a structure including a central polymer portion including a polyalkoxide and terminal methylene malonate groups having one or more (or all) of the features illustrated below:

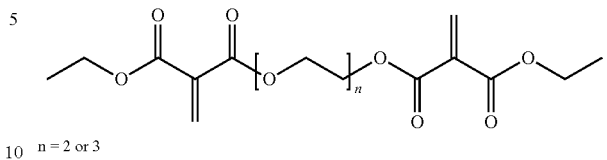

n = 2 or 3

Example 11

Example 11 is a reaction mixture including a glycerol ethoxylate end-capped with a methylene malonate monomer and unreacted methylene malonate monomer. The end-capping of the glycerol ethoxylate may be carried out using a transesterification process.

A 250 mL round bottom flask is charged with about 30 g (about 0.17 mol) of DEMM, about 3 g (about 10 parts per 100 parts of DEMM) of enzyme NOVOZYME 435 *candida antarctica* isoform B (commercially available from NOVOZYME) and about 56 g (about 0.056 mol) of glycerol ethoxylate (having a number average molecular weight of about 1000, obtained from Sigma Aldrich). The flask is connected to a rotary evaporator with reduced pressure of about 200 mm Hg and is heated to about 55° C. for about 8 hours. Ethanol is removed as a reaction byproduct. The enzyme is then filtered from the product using cotton plug in a 20 ml syringe, for isolating the reaction mixture. NMR results are obtained of the reaction mixture and used to calculate the conversion of the glycerol ethoxylate to the end-capped product. About 40% of desired transesterified products (i.e., end-capped product) is observed. The NMR spectrum for the reaction mixture is shown in FIG. 6. It is believed that the reaction mixture includes disubstituted and trisubstituted glycerol ethoxylate reaction products. The resulting reaction mixture includes end-capped glycerol ethoxylate having one or more of the features as shown in the structures below.

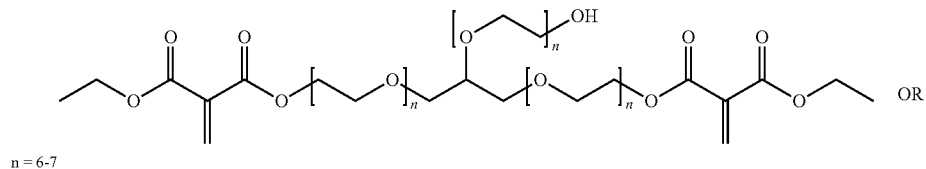

n = 6-7

OR

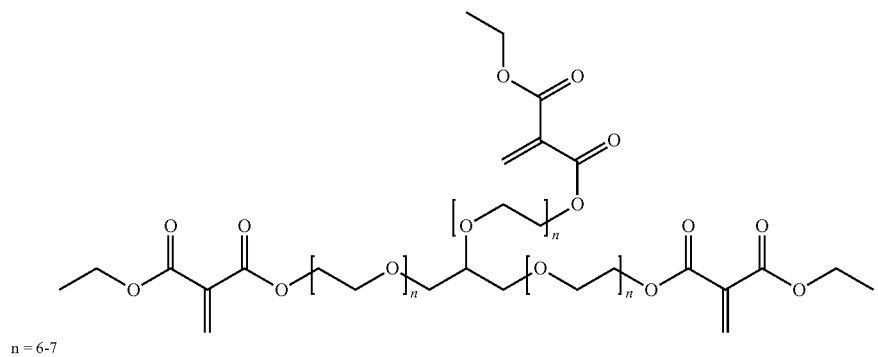

n = 6-7

The reaction mixture is drawn down on a pre-initiated (0.1% Na-benzoate in butyl cellosolve) cold rolled steel panel using a Meyer Rod 10 resulting in a about 25-micron thick coating after full cure at room temperature for about 24 hours followed by heating at about 82° C. for about 1 hour. The coating displays hydrophilic character with water wetting the surface with ease and eventually permeating through the coating layer on continued exposure. In comparison, a specimen prepared with the reaction mixture replaced with only DEMM and cured under the same conditions (e.g., resulting in a DEMM homopolymer) demonstrates no hydrophilic character. Thus, the end-capped glycerol ethoxylate is demonstrates may be used to impart hydrophilicity in a coating (e.g., in a methylene malonate coating, such as a DEMM based coatings).

Example 12

A polymerizable composition may be prepared by combining the reaction mixture of diol and a methylene malonate with one or more additional monomers and/or one or more crosslinkers. As an example, Example 12 is prepared by mixing the reaction mixture of Example 11 with dimethyl methylene malonate (i.e., D3M), additional DEMM, and 1,5 pentanediol DEMM crosslinker in the amounts shown in the Table below.

| Monomers/Oligomer | Amount (%) |
| --- | --- |
| D3M | 30 |
| DEMM | 6 |
| 1,5 pentanediol DEMM crosslinker | 14 |
| Reaction mixture from Example 9 | 50 |

The polymerizable composition is drawn down on a pre-initiated (0.1% Na-benzoate in butyl cellosolve) cold rolled steel panel using a Meyer Rod 10 resulting in a 25-micron thick coating after full cure at room temperature for about 24 hours followed by heating at about 82° C. for about 1 hour. The coating does not display the hydrophilic behavior seen above for example 11. This is believed to be due to the high amount of crosslinking offered by the pentane diol crosslinker. By adjusting the amount of the polyol portion (e.g., the glycerol ethoxylate) in the final coating through formulating, it may possible to obtain antifouling characteristics, while maintaining a durable, water resistant coating.

Urethane/Carbamate Link

The end-capped compound may include a urethane or carbamate linkage. Such a structure may be prepared using a reaction that includes an isocyanurate. Such a structure may be prepared by a method that avoids the need for any isocyanurate or isocyanates. For example, the carbamate linkage may be obtained by reacting a cyclic carbonate with an amine (e.g., a compound having one or more, two or more, or three or more amine groups) to form a carbamate linkage and a terminal alcohol. The terminal alcohol may then be used to end cap the carbamate containing compound with a 1,1-disubstituted alkene compound (e.g., via a transesterification reaction). Preferably each of the amine groups results in a carbamate group and is endcapped with a 1,1-disubstituted alkene compound.

Example 13

Example 13 is a reaction mixture including an isocyanurate ethoxylate end-capped with a methylene malonate monomer and unreacted methylene malonate monomer. The end-capping of the isocyanurate may be carried out using a transesterification process.

A 250 mL round bottom flask having a distillation head, thermometer, vacuum adapter, collection flask and mechanical stirrer is charged with a mixture of about 200 g (about 1.16 moles) of DEMM and about 0.4 g (about 2000 ppm) of BHT (i.e., butylated hydroxytoluene). The mixture is heated and when the temperature reaches about 40° C. about 0.6 ml of a 1 mole % sulfuric acid is added to the round bottom flask using a syringe. Next, about 1.0 equivalents (50.6 grams equal to about 1.94 moles) of 1,3,5-Tris(2-hydroxyethyl)isocyanurate is added in parts into the flask. The reactants and one of the desired products are shown in the equation below:

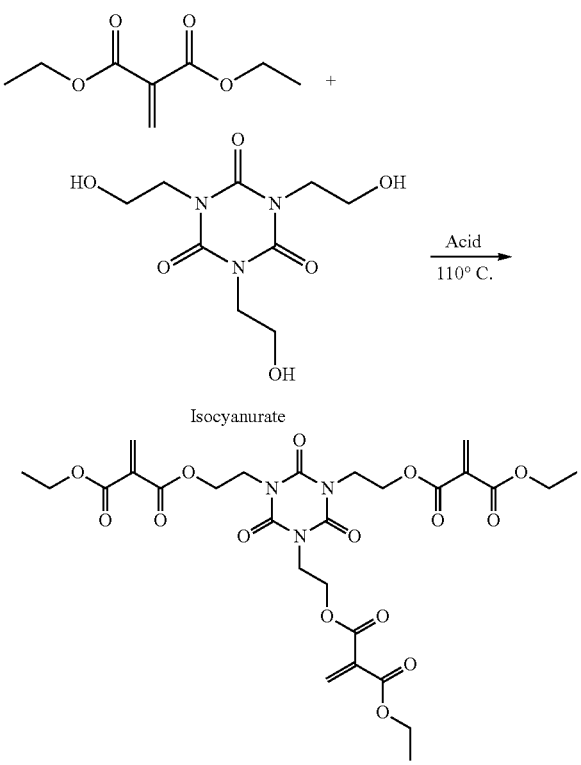

Figure 7:
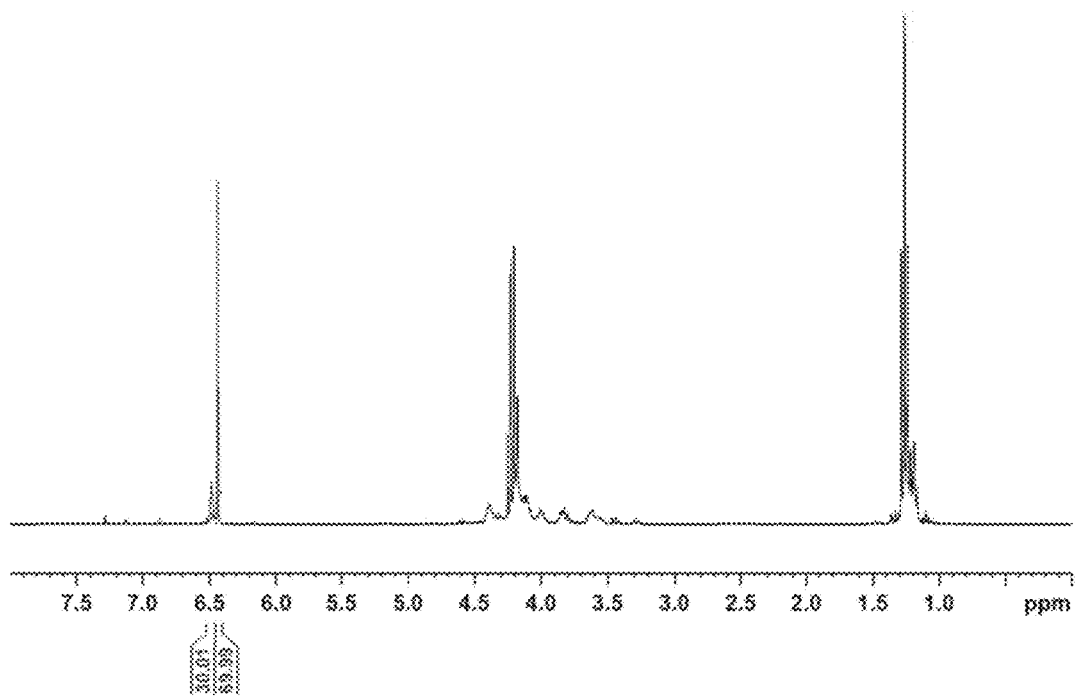
FIG. 7 is an illustrative proton NMR spectrogram of a reaction mixture including an end-capped isocyanurate.

The reaction is carried at a temperature of about 110° C., at a reduced pressure of about 500 mm Hg, with vigorous stirring, for about 3 hours. Ethanol is collected as the reaction byproduct. After the reaction, the reaction mixture is analyzed using H NMR, as shown in FIG. 7. The conversion of the isocyanurate to the end-capped analog is about 30 percent.

Example 14

A compound including carbamate linkages may be prepared without isocyanates, by first reacting a cyclic carbonate with one or more amine groups to obtain a compound having one or more carbamate group and one or more hydroxyl groups. The hydroxyl groups are then reacted to attach a 1,1-disubstituted alkene compound. For example, the process may include a first step of reacting a cyclic carbonate with a diamine using a ring opening reaction to obtain a di-urethane diol. Preferred cyclic carbonates include ethylene carbonate and propylene carbonate. The reaction may include one or any combination of the features illustrated below:

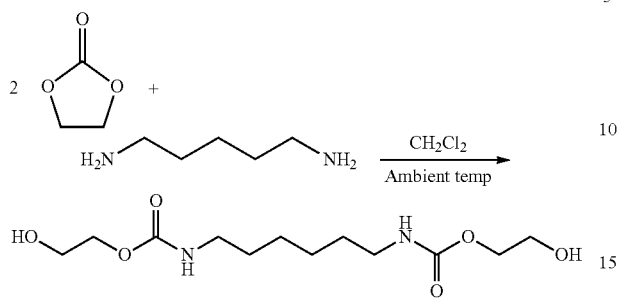

The reaction of the carbamate containing polyol with a 1,1-disubstituted alkene compound may include one or any combination of the features listed below:

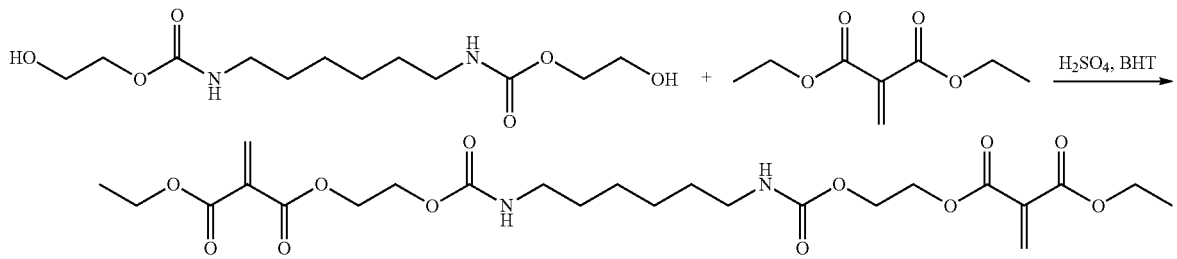

The resulting end capped compound preferably includes a plurality of carbamate linkages and spaced apart alkene groups. It will be appreciated that the spacing of the alkene groups may be controlled by the length of the amine starting material. For example, two amine groups may be spaced apart by 4 or more, 6 or more, 10 or more, 15 or more, or 20 or more carbon atoms.

Figure 8:
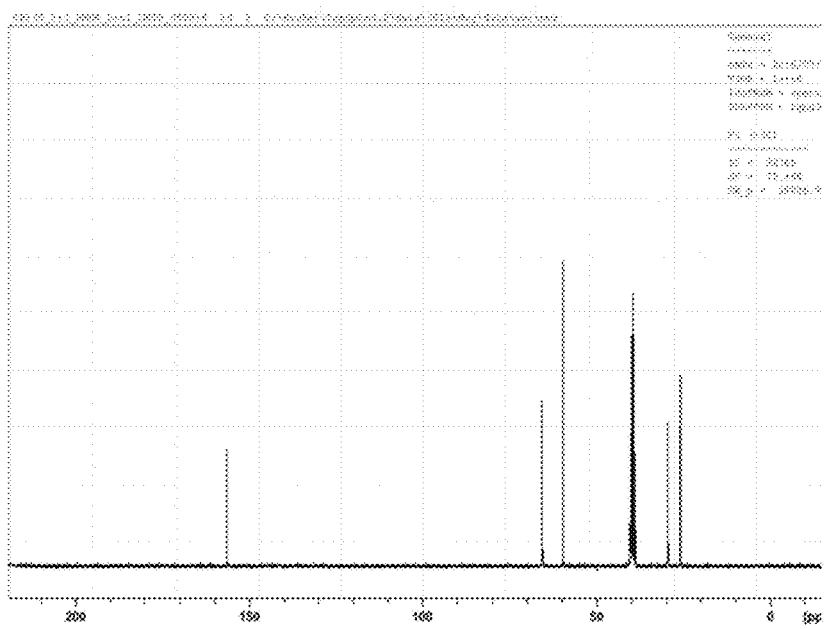
FIG. 8 is an illustrative $^{13}$C-NMR spectrogram of an intermediate diol.

Example 14 is prepared by dissolving ethylene carbonate (e.g., about 26.5 g, 0.30 mole, 2.0 equivalents) in dichloromethane (about 150 ml). An initial endotherm is observed during the dissolution and the temperature drops from about 23° C. to about 0.2° C. Hexamethylenediamine (about 17.51 g, 0.15 mol, 1.0 equiv) is then added to the solution. A slight exotherm of about 10-12° C. is observed. The solution is reacted and stirred for 3 hours during which the temperature increases to about 27° C. and the solution becomes turbid. The reaction is then continued at about 30° C. for an additional hour with stirring. The reaction product is insoluble in the solvent and crashes out of the solution. The suspension is then filtered and washed multiple times to remove unreacted starting materials. FIG. 8 shows an $^{13}C$ NMR spectrogram of the diol intermediate.

Figure 9:
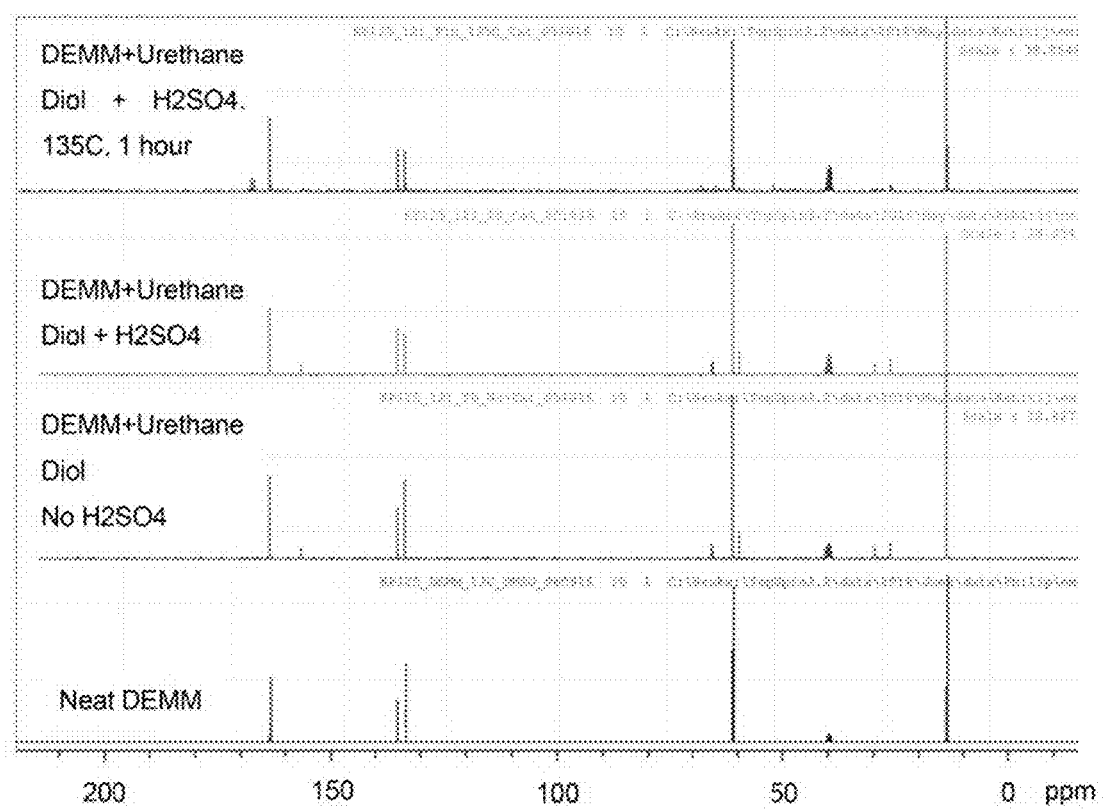
FIG. 9 is an illustrative $^{13}$C-NMR spectrum of (a) neat DEMM, (b) DEMM and a urethane diol (no sulfuric acid), (c) DEMM, a urethane diol, and sulfuric acid, and (d) DEMM, a urethane diol, and sulfuric acid after reacting for 1 hour at 135° C.

The solid di-urethane diol filtrate is then reacted with DEMM as described below. DEMM (31 g, 0.18 mol, 5.96 equiv) and BHT (0.05 g) is charged into a 3 necked round bottom flask fitted with a thermocouple and a vacuum take off adapter. The solid di-urethane diol (8.8 g, 0.030 mol, 1.0 equiv) is then added to the flask. The flask is then heated to ~130-135° C. While the flask is being heated sulfuric acid (0.1 mL) is added by a syringe. The reaction is then stirred under reduced pressure (~190 mmHg), for efficient removal of the ethanol byproduct. At temperatures above about 70° C., the suspension (i.e., the di-urethane diol) dissolves to give a clear solution having a faint to dark yellow color. The solution is then stirred for about 1 to 1.5 hours and then allowed to cool under reduced pressure. Solid particulates are observed and filtered. The reaction is monitored using $^{13}C$ NMR, as illustrated in FIG. 9. FIG. 9A illustrates the 13C NMR spectrogram of neat DEMM. FIG. 9B illustrates the mixture of the DEMM and the Urethane diol, prior to adding the sulfuric acid. FIG. 9C illustrates the mixture after adding the sulfuric acid. FIG. 9D illustrates the spectrogram of the mixture after reacting for 1 hour at 135° C.

What is claimed is:

1. A functionalized polyhydric compound comprising:
an isocyanurate trimer polyol, an aromatic polyester polymer polyol, or a siloxane-containing polymer polyol wherein the polyols have an alcohol group at least both ends of the polyol, wherein at least one of the alcohol groups is capped with a 1,1-disubstituted alkene compound, wherein one or both of the disubstituted groups of the alkene includes an ester group.

2. The functionalized polyhydric compound of claim 1, wherein the number of 1,1-disubstituted alkene compounds is two or more.

3. The functionalized polyhydric compound of claim 1, wherein each the 1,1-disubstituted 1-alkene compound(s) is attached to the polyol by an ester linkage.

4. The functionalized polyhydric compound of claim 1, wherein the 1,1-disubstituted alkene is a 1,1-disubstitued ethylene having a carbon atom that is doubly bonded to another carbon atom, wherein the carbon atom is further bonded to two carbonyl groups.

5. The functionalized polyhydric compound of claim 4, wherein the 1,1-disubstituted alkene includes one or more additional carbon atoms that are each doubly bonded to another carbon atom and further bonded to two carbonyl groups.

6. The functionalized polyhydric compound of claim 4, wherein the 1,1-disubstituted alkene compound is a methylene malonate.

7. The functionalized polyhydric compound of claim 1, wherein the 1,1-disubstituted alkene monomer is a 1,1-disubstituted ester having the structure:

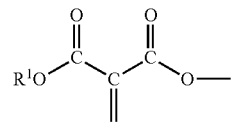

wherein $R^1$ is separately in each occurrence a hydrocarbyl group which may contain one or more heteroatoms.

8. The functionalized polyhydric compound of claim 1, wherein the polyol is a carbinol terminated siloxane, wherein the number of siloxane units is about 3 or more.

9. The functionalized polyhydric compound of claim 1, wherein the functionalized polyhydric compound includes carbamate linkages connecting the 1,1, disubstituted alkene compound(s) to the polyol.

10. A method comprising the steps of:
mixing the polyol of claim 1, and a 1,1-disubstituted alkene compound; and
reacting the polyol with the 1,1-disubstitiuted alkene compound wherein at least one of the disubstituted groups is an ester.

11. A method comprising the step of cross-linking the functionalized polyhydric compound of claim 1.

12. A polymer prepared by polymerizing a composition including one or more 1,1-disubstituted alkene compounds and the functionalized polyhydric compound of claim 1, wherein the composition includes a sufficient amount of the polyol and a sufficient amount of the 1,1-disubstituted alkene compound(s) so that the polymer exhibits two different glass transition temperatures, which are different by about 20° C. and/or two different melting temperatures, which are different by about 20° C. with one glass transition temperature and/or melting temperature associated with the polyol and one glass transition temperature and/or melting temperature associated with a polymethylene malonate.

13. A method of forming the functionalized polyhydric compound of claim 1 comprising the steps of:
continuously feeding a 1,1-disubstituted compound into a reactor;
continuously feeding the polyol into the reactor;
wherein continuous flow reaction of the 1,1-disubstituted compound and the polyol in the presence of a catalyst forms the functionalized polyhydric compound via a transesterification reaction.

14. The functionalized polyhydric compound of claim 1, wherein the 1,1-disubstituted alkene has the structure:

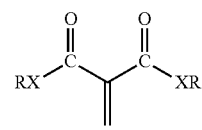

wherein R is a hydrocarbyl group which may contain one or more heteroatoms and X is oxygen or a direct bond, wherein at least one X is oxygen.

15. The polymer of claim 12, wherein the polymer is used a film or a coating.

* * * * *